US006963805B2

(12) United States Patent
Frazer et al.

(10) Patent No.: US 6,963,805 B2
(45) Date of Patent: Nov. 8, 2005

(54) METHODS FOR IDENTIFYING THE EVOLUTIONARILY CONSERVED SEQUENCES

(75) Inventors: Kelly A. Frazer, San Mateo, CA (US); Nila Patil, Woodside, CA (US); John Sheehan, Mountain View, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 0 days.

(21) Appl. No.: 09/972,595

(22) Filed: Oct. 5, 2001

(65) Prior Publication Data

US 2003/0017474 A1 Jan. 23, 2003

Related U.S. Application Data

(60) Provisional application No. 60/284,436, filed on Apr. 18, 2001.

(51) Int. Cl.[7] ............... G01N 33/48; G01N 33/50; G06F 19/00
(52) U.S. Cl. ............... 702/20; 702/19; 435/6
(58) Field of Search ............... 435/6; 702/19, 702/20

(56) References Cited

U.S. PATENT DOCUMENTS

| | | | |
|---|---|---|---|
| 5,405,783 A | 4/1995 | Pirrung et al. | 436/518 |
| 5,800,992 A | 9/1998 | Fodor et al. | 435/6 |
| 5,837,832 A | 11/1998 | Chee et al. | 526/22.1 |
| 5,925,525 A | 7/1999 | Fodor et al. | 435/6 |
| 5,968,740 A | 10/1999 | Fodor et al. | 435/6 |
| 6,013,449 A | 1/2000 | Hacia et al. | 435/6 |
| 6,251,601 B1 | 6/2001 | Bao et al. | |
| 6,383,742 B1 | 5/2002 | Drmanac et al. | |
| 6,391,550 B1 | 5/2002 | Lockhart et al. | |

FOREIGN PATENT DOCUMENTS

| | | |
|---|---|---|
| EP | 0785280 A2 | 7/1997 |
| EP | 0848067 A2 | 6/1998 |
| WO | WO 95/00530 A1 | 1/1995 |

OTHER PUBLICATIONS

Frazer et al., Genome Research, 11:1651–1659, 2001.*
Hacia, J.G., et al.; Detection of Heterozygous Mutations in BRCA1 Using High Density Oligonucleotide Arrays and Two–Colour Fluorescence Analysis, Nature Genetics, 1996, 14:4:441–447.
Loots et al., "Identification of a Coordinate Regulator of Interleukins 4, 13, and 5 by Cross–Species Sequence Comparisons", Science, vol. 288 pp. 136–140 (Apr. 7, 2000).
Murphy et al., "Database Searches for Binding Sites", Science, vol. 288 (5475) pp 2319 ;(Jun. 30, 2000).
Oeltjen, J.C. et al., "Large–Scale Comparative Sequence Analysis of the Human and Murine Bruton's Tyrosine Kinase Loci Reveals Conserved Regulatory Domains" Genome Research; 7:315–329 (1997).

(Continued)

*Primary Examiner*—Marianne P. Allen
(74) *Attorney, Agent, or Firm*—Deana A. Arnold; Gulshan H. Shaver

(57) ABSTRACT

The present invention provides methods for determining sequence similarity (conserved sequences) between nucleic acids from a first organism and nucleic acids from a second, different organism without having to know a priori the nucleic acid sequence from the second, different organism. The first nucleic acid can be from any organism where the sequence of the nucleic acid is known and the second nucleic acid can be from any organism. The method involves determining which bases from the second nucleic acid are identical to the first nucleic acid, and allows one to determine the sequence of portions of the second nucleic acid. The invention is useful for identifying putative functional regions or putative organism-sequences in a genome.

12 Claims, 7 Drawing Sheets

OTHER PUBLICATIONS

Hardison, R.C. et al., "Long Human–Mouse Sequence Alignments Reveal Novel Regulatory Elements: A Reason to Sequence the Mouse Genome", Genome Research; 7:959–966 (1997).

Karet, G. et al., "Unraveling Human Diversity", The SNP Consortium; S5–S12, Nov./Dec. 2000.

Hinde, A., "Evolution, not Revolution" Trends Biotechnol.; 18:230–231 (2000).

Cargill, M. et al., "Mining for SNPs: Putting the Common Variants–Common Diease Hypothesis to the Test", Pharmacogenomics; 1–27–37 (2000).

Wang, D.G. et al., "Large–Scale Identification, Mapping, and Genotyping of Single Nucleotide Polymorphisms in the Human Genome", Science; 280:1077–1082 (1998).

Pennacchio, L.A. et al., "Genomics Strategies to Identify Mammalian Regulatory Sequences", Nature; 2:100–109 (2001).

Wynn, S.L. et al., "Organization and Conservation of the GART/SON/DONSON Locus in Mouse and Human Genomes", Genomics; 68:57–62 (2000).

Wiltshire, T. et al., "Perfect Conserved Linkage Across the Entire Mouse Chromosome 10 Region Homologous to Human Chromosome 21"Genome Research; 9:1214–1222 (1999).

Ansari–Lari, M. A. et al., "Comparative Sequence Analysis of a Gene–Rich Cluster at Human Chromosome 12p13 and its Syntenic Region in Mouse Chromosome 6"Genome Research; 8:29–40 (1998).

Onyango, P. et al., "Sequence and Comparative Analysis of the Mouse 1–Megabase Region Orthologous to the Human 11p15 Imprinted Domain", Genome Research; 10:1697–1710 (2000).

Hardison, R., "Conserved Noncoding Sequences are Reliable Guides to Regulatory Elements", Trend Genet,; 16–369–72 (2000).

Dubchak, I. et al., "Active Conservation of Noncoding Sequences Revealed by Three–Way Species Comparisons", Genome Research; 10:1304–1306 (2000).

Hacia, J.G. et al., "Determination of Ancestral Alleles for Human Single–Nucleotide Polymorphisms Using High–Density Oligonucleotide Arrays", Nature Genetics; 22:164–167 (1999).

Hacia, J.G. et al., "Evolutionary Sequence Comparsions Using High–Density Oligonucleotide Arrays", Nature Genetics; 18:155–158 (1998).

Chen et al., "Genomic Divergences Between Humans and Other Hominoids and the Effective Population Size of the Common Ancestor of Humans and Chimpanzees," Am. J. Hum. Genet. 68:444–456, 2001.

Fujiyama et al., "Construction and Analysis of a Human–Chimpanzee Comparative Clone Map," Science, vol. 295, pp. 131–134, Jan. 4, 2002.

Gagneux et al., "Genetic Differences between Humans and Great Apes," Molecular Phylogenetics an Evolution, vol. 18, No. 1, pp. 2–13, Jan. 2001.

Hacia et al., "Genome of the apes", Trends in Genetics, vol. 17, No. 11, pp. 637–645, Nov. 2001.

Hattori et al., "The DNA sequence of human chromosome 21," Nature, vol. 405, pp. 311–319, May 18, 2000.

King et al., "Evolution at Two Levels in Humans and Chimpanzees," Science, vol. 188, No. 4184, pp. 107–116, Apr. 11, 1975.

Koop et al., "A Molecular View of Primate Phylogeny and Important Systematic and Evolutionary Questions," Mol. Biol. Evol. 6(6):580–612. pp. 580–612, 1989.

Nickerson et al., "Molecular Definition of Pericentric Inversion Breakpoints Occurring during the Evolution of Humans and Chimpanzees," Genomics 50, 368–372 (1998).

Ueda et al., "Human–Specific Sequences: Isolation of Species–Specific DNA Regions by Genome Subtraction," Genomics 8, 7–12 (1990).

Yunis et al. "The Origin of Man: A Chromosomal Pictorial Legacy," Science, vol. 215, pp. 1525–1530, Mar. 19, 1982.

* cited by examiner

Reference sequence

AGCCTTAAGAAACTTGGCTCAGGTG (SEQ ID NO: 1)

TCGGAATTCTTTAAACCGAGTCCAC   Probe - noncomplementary at central position (SEQ. ID. NO: 2)
TCGGAATTCTTTCAACCGAGTCCAC   Probe - noncomplementary at central position (SEQ. ID. NO: 3)
TCGGAATTCTTTGAACCGAGTCCAC   Probe - complementary (SEQ. ID. NO: 4)
TCGGAATTCTTTTAACCGAGTCCAC   Probe - noncomplementary at central position (SEQ ID NO: 5)

Figure 2

SEQUENCE LISTING

<160> NUMBER OF SEQ ID NOS: 9

<210> SEQ ID NO 1
<211> LENGTH: 25
<212> TYPE: DNA
<213> ORGANISM: Human

```
<400> SEQUENCE: 1
agccttaaga aacttggctc aggtg                                    25

<210> SEQ ID NO 2
<211> LENGTH: 25
<212> TYPE: DNA
<213> ORGANISM: Human

<400> SEQUENCE: 2
tcggaattct ttaaaccgag tccac                                    25

<210> SEQ ID NO 3
<211> LENGTH: 25
<212> TYPE: DNA
<213> ORGANISM: Human

<400> SEQUENCE: 3
tcggaattct ttcaaccgag tccac                                    25

<210> SEQ ID NO 4
<211> LENGTH: 25
<212> TYPE: DNA
<213> ORGANISM: Human

<400> SEQUENCE: 4
tcggaattct ttgaaccgag tccac                                    25

<210> SEQ ID NO 5
<211> LENGTH: 25
<212> TYPE: DNA
<213> ORGANISM: Human

<400> SEQUENCE: 5
tcggaattct tttaaccgag tccac                                    25

<210> SEQ ID NO 6
<211> LENGTH: 30
<212> TYPE: DNA
<213> ORGANISM: Human

<400> SEQUENCE: 6
tgtcggaatt ctttgaaccg ggtccacata                               30

<210> SEQ ID NO 7
<211> LENGTH: 30
<212> TYPE: DNA
<213> ORGANISM: Human

<400> SEQUENCE: 7
ggaaggccca ctacaccgaa aacactgacg                               30

<210> SEQ ID NO 8
<211> LENGTH: 30
<212> TYPE: DNA
<213> ORGANISM: Human

<400> SEQUENCE: 8
tgtcggaatt ctttgaaccg agtccacata                               30

<210> SEQ ID NO 9
<211> LENGTH: 30
<212> TYPE: DNA
<213> ORGANISM: human
```

```
<400> SEQUENCE: 9
aaaccttgtg ctacaccgaa aacactgtat                                      30
```

METHODS FOR IDENTIFYING THE EVOLUTIONARILY CONSERVED SEQUENCES

RELATED APPLICATIONS

This application claims priority to provisional application U.S. Ser. No. 60/284,436 filed Apr. 18, 2001, which is incorporated by reference in its entirety for all purposes.

BACKGROUND OF THE INVENTION

The sequence of the complete human genome is now available. To take full advantage of this genomic sequence data, it is necessary to use computational and/or experimental methods to distinguish sequences that have biological function from those that do not. For example, it is estimated that only 5% of the human genome contains coding regions. The value of identifying coding sequence is clear as variation in coding sequences can have a direct impact on the encoded protein and the functionality of the gene; thus, there is a tremendous effort in the genomics community to identify such coding sequences. However, in addition to coding sequences, there are non-coding sequences in the genome that have great importance in determining gene function. These important non-coding sequences contain regulatory regions, such as promoters, enhancers, ribosome binding sites, transcription termination sites and the like. Sifting through the 95% of the genome comprised of non-coding sequences to identify the small fraction of non-coding elements with biological importance is an even greater challenge than identifying genes. Therefore, methods to identify rapidly putative functional, non-coding sequences in the human genome or the genome of any organism are needed.

Conversely, it is of interest to understand and study how very closely related organisms differ from one another genetically. Such organism-differentiating sequences are what give a particular organism unique characteristics. For example, comparison of the genomes of two closely-related corn hybrids may allow one to identify the genetic sequence that makes one of the hybrids robust even in times of draught or resistant to a particular parasite.

Thus, it is of great interest in the field of genetics to determine the sequences of the genomes of many different organisms and identify functional regions and organism-differentiating sequences therein. One way to identify such sequences is by comparing the sequence of one organism to another. However, in methods known to date, in order to make such comparisons both sequences must be known. Though a great deal of sequencing has been done for many organisms in the past 10 years, the entire genomes of only a handful of organisms is known.

SUMMARY OF THE INVENTION

The present invention provides methods for determining sequence similarity between nucleic acids from a first organism and nucleic acids from a second, different organism without having to know a priori the nucleic acid sequence from the second, different organism. The first nucleic acid can be from any organism where the sequence of the nucleic acid is known and the second nucleic acid can be from any organism. The method involves determining which bases from the second nucleic acid are identical to the first nucleic acid, and allows one to determine the sequence of the portions of the second nucleic acid that are similar to the first nucleic acid. The invention is useful to screen for functional regions or organism-differentiating sequences in a genome.

One aspect of the present invention provides a method for determining sequence similarity between nucleic acids from a first organism and a second organism, comprising the steps of: providing a substrate having a plurality of detection probes complementary and non-complementary to the known nucleic acid sequence from the first organism, wherein each detection probe is at a known location; contacting sample nucleic acids from the second organism to the substrate under conditions which allow hybridization of substantially complementary sample nucleic acids to detection probes to produce hybridized detection probes; determining the location of the hybridized detection probes; and identifying sequences of the hybridized detection probes by referring to the location of said hybridized detection probes; wherein when the sequences of the hybridized detection probes are the same as a sequence complementary to the known nucleic acid sequence from the first organism, there is sequence similarity between nucleic acids from the first organism and the second organism.

Another aspect of the present invention provides a method to screen for functional sequences in nucleic acids of a first organism, comprising the steps of: providing a substrate having a plurality of detection probes complementary and non-complementary to known nucleic acid sequence from the first organism, wherein each detection probe is at a known location; contacting sample nucleic acids from a second. organism to the substrate under conditions which allow hybridization of substantially complementary sample nucleic acids to detection probes to produce hybridized detection probes, wherein the first organism and the second organism diverged evolutionarily between about 60 million years ago and about 120 million years ago; determining a location of the hybridized detection probes; and identifying sequences of the hybridized detection probes by referring to the location of the hybridized detection probes; wherein when the sequences of the hybridized detection probes are the same as a sequence complementary to the known nucleic acid sequence from the first organism there is sequence similarity between the nucleic acids from the first organism and the second organism, and regions in the nucleic acids of the first organism where there is sequence similarity with the nucleic acids from the second organism are functional regions in the nucleic acids of the first organism.

An additional aspect of the present invention provides a method to screen for functional sequences in nucleic acids of an additional first organism, comprising the steps of: providing a first substrate having a plurality of detection probes complementary and non-complementary to a known nucleic acid sequence from the first organism, wherein each detection probe is at a known location; contacting sample nucleic acids from a second organism to the first substrate under conditions which allow hybridization of substantially complementary sample nucleic acids to detection probes to produce hybridized detection probes; determining a location of the hybridized detection probes; identifying sequences of the hybridized detection probes by referring to the location of the hybridized detection probes; wherein when the sequences of the hybridized detection probes are the same as a sequence complementary to the known nucleic acid sequence from the first organism there is sequence similarity between the nucleic acids from the first organism and the second organism; providing a second substrate having a plurality of detection probes complementary and non-complementary to a known nucleic acid sequence from the first organism, wherein each detection probe is at a known location; contacting sample nucleic acids from a third organism to the second substrate under conditions which allow hybridization of substantially complementary sample nucleic acids to detection probes to produce hybridized detection probes; determining a location of the hybridized detection probes; identifying sequences of the hybridized detection probes by referring to the location of the hybridized detection probes; wherein when the sequences of the hybridized detection probes are the same as a sequence complementary to the known nucleic acid sequence from the first organism there is sequence similarity between the nucleic acids from the first organism and the third organism; determining the regions in the nucleic acids of the first organism where there is sequence similarity both with the nucleic acids from the second organism and the nucleic acids from the third organism, wherein the first organism and at least one of the second organism and the third organism diverged evolutionarily between about 60 million years ago and about 120 million years ago, and wherein regions in the nucleic acids from the first organism having sequence similarity with both the nucleic acids from the second organism and the third organism are functional regions in the nucleic acid of the first organism.

An additional aspect of the present invention provides a method to screen for organism-differentiating sequences in nucleic acids of a first organism, comprising the steps of: providing a substrate having a plurality of detection probes complementary and non-complementary to a known nucleic acid sequence from the first organism, wherein each detection probe is at a known location; contacting sample nucleic acids from a second organism to the substrate under conditions which allow hybridization of substantially complementary sample nucleic acids to detection probes to produce hybridized detection probes, wherein the first organism and the second organism are genetically closely related; determining a location of the hybridized detection probes; and identifying sequences of the hybridized detection probes by referring to the location of the hybridized detection probes; wherein when the sequences of the hybridized detection probes are the same as a sequence complementary to the known nucleic acid sequence from the first organism there is sequence similarity between the nucleic acids from the first organism and the second organism, and regions in the nucleic acids of the first organism where there is sequence divergence with the nucleic acids from the second organism are organism-differentiating sequences in the nucleic acids of the first and second organisms. One embodiment of this aspect of the invention provides that the second organism diverged from the first organism less than about 60 million years ago.

A further aspect of the present invention provides a method for determining a sequence of nucleic acids from a second organism, comprising the steps of: providing a substrate having a plurality of detection probes complementary and non-complementary to a known nucleic acid sequence from a first organism, wherein each detection probe is at a known location; contacting sample nucleic acids from the second organism to the substrate under conditions which allow hybridization of substantially complementary sample nucleic acids to detection probes to produce hybridized detection probes; determining a location of the hybridized detection probes; and identifying sequences of the hybridized detection probes by referring to the location of the hybridized detection probes, whereby the sequence of nucleic acids from the second organism can be determined by having identified the sequences of the hybridized detection probes. In addition, this particular aspect of the present invention may comprise the further step of performing reverse PCR on the hybridized sample nucleic acids to produce reverse PCR fragments, and may include an even further step of sequencing the produces reverse PCR fragments.

An additional aspect of the present invention provides a method for identifying genomic regions where polymorphisms may have phenotypic effect in a first organism, comprising the steps of: providing a substrate having a plurality of detection probes complementary and non-complementary to a known nucleic acid sequence from the first organism, wherein each detection probe is at a known location; contacting sample nucleic acids from a second organism to the substrate under conditions which allow hybridization of substantially complementary sample nucleic acids to detection probes to produce hybridized detection probes, wherein the first organism and the second organism diverged evolutionarily between about 60 million years ago and about 120 million years ago; determining a location of the hybridized detection probes; and identifying sequences of the hybridized detection probes by referring to the location of the hybridized detection probes; wherein when the sequences of the hybridized detection probes are the same as a sequence complementary to the known nucleic acid sequence from the first organism there is sequence similarity between the nucleic acids from the first organism and the second organism, and regions in the nucleic acids of the first organism where there is sequence similarity with the nucleic acids from the second organism are regions where polymorphisms may have phenotypic effect in the first organism.

In the aforementioned aspects of the present invention, the nucleic acids from the first organism, the second organism and the third organism (if any) may be genomic DNA. In addition, the methods may employ arrays where the plurality of probes are at a density of at least 100 probes/$cm^2$, at least 1,000 probes/$cm^2$ or at least 10,000 probes/$cm^2$ or more. Further, the plurality of probes on the arrays employed in the methods of the current invention may be sets of four probes where one probe of the probe set is perfectly complementary to the known nucleic acid sequence and three probes of the probe set are non-complementary to the known nucleic acid sequence, and the non-complementary probes differ from the known nucleic acid sequence by one base. Further, the non-complementary one base of the probe may be a base located at or near a central position of the probe. In addition, the plurality of probes may be at least 18 bases long, at least 20 bases long, or at least 25 bases long or more.

In addition, the aforementioned aspects of the present invention may employ techniques where the sample nucleic acids are nucleic acids which have been amplified by the polymerase chain reaction. In certain aspects of the present invention, at least one primer for the polymerase chain reaction has characteristics selected from the group consisting of not being degenerate; being derived from a human nucleic acid sequence, being comprised of about 50% GC content, being greater than about 25 nucleotides in length, and a combination thereof. In specific embodiments, at least one primer for said polymerase chain reaction is at least about 50 $\mu$M in concentration, at least about 75 $\mu$M in concentration, or at least about 100 $\mu$M in concentration. In another specific embodiment, the polymerase chain reaction comprises a first series of a first number of cycles at a first temperature for annealing of a primer followed by a second series of a second number of cycles at a second temperature for annealing of a primer. In a further specific embodiment, the first number of cycles is about ten. In another specific embodiment, the first temperature for annealing of a primer is greater than said second temperature for annealing of a primer. In an additional specific embodiment, the second number of cycles is about thirty.

Further, in the aforementioned aspects of the present invention, a step of calculating an identity index between sub-regions of the nucleic acids from the first organism and the nucleic acids from the second organism or the third organism may be employed. The identity index may be calculated by determining a percentage of similarity between sub-regions of the nucleic acids from the first organism and the nucleic acids from the second or third organism. In addition, the methods may designate the sub-regions as overlapping, moving windows of base pairs across the nucleic acid sequence from a first organism, wherein the windows are between about 20 base pairs and 150 base pairs, the overlap of the windows is between about 5 base pairs and about 75 base pairs. One application of the present invention designated windows of 30 base pairs and an overlap of 10 base pairs.

One application of the present invention is to use human genomic sequence as the reference or known sequence. Human genomic sequence is one of the few complete genomic sequences known to date. However, it should be understood that the methods of the present invention can be used with any organisms as long as a sequence of nucleic acids is known from at least one of the organisms. In certain applications of the present invention, mouse and dog sequences were representative for organisms having diverged from humans between about 60 and 120 million years ago, and gorilla and chimp sequences were representative for organisms having diverged from humans less than about 60 million years ago.

A further aspect of the present invention provides a computer system comprising: a module that receives a plurality of hybridization intensities wherein each of the intensities reflects the hybridization of one of a plurality of probes from a first nucleic acid sequence from a first organism to a sample nucleic acid from a second organism, wherein the probes are complementary and non-complementary to a known nucleic acid sequence from the first organism, wherein the probes are arrayed on a substrate and wherein each detection probe is at a known location on the substrate; a module that identifies bases of the plurality of probes according to the hybridization intensities; a module that calculates an identity index between the first nucleic acid sequence from the first organism and the sample nucleic acid from the second organism; and a module for storing and retrieving hybridization intensities and identity indices onto a computer readable media. The hybridization intensities may be stored in the memory of the computer or onto a storage media. A processor of the computer (or multiple processors if the computer or computers are so configured) executes the aforementioned modules. A database may be utilized for the management of the hybridization intensity data and interpretive results of the software.

Nucleic acid arrays, well known in the art, are particularly useful for genomic DNA comparisons. Typically, the detection probes are immobilized on a substrate at a density of at least 100 probes/$cm^2$, preferably at a density of at least 1000 probes/$cm^2$, and more preferably a density of at least 10000 probes/$cm^2$. The detection probes typically comprise four probes for each base position on each single DNA strand to be interrogated; however, probe sets of other sizes may be used. The detection probes may be synthesized using photo-directed synthesis using a shift mask strategy or using individually addressable micro-mirror arrays, or by other methods known in the art. Typically, the probes are oligo-nucleotides of at least 18 bases, preferably at least 20 bases, and more preferably at least 25 bases.

The nucleic acid sample may be prepared in any method known by those with skill in the art. For closely-related organisms, typically the genomic DNA sample is prepared by extraction of genomic DNA from the second organism, followed by long range amplification of the DNA by the polymerase chain reaction using primers based on the reference sequence. For less related organisms, it may be necessary to sub-clone portions of the genomic DNA of the second organism into a cloning vector before amplification. In the case of screening for functional regions of a human genome, the second organism may be a mammal such as canine, rodent, ungulate or lower primate. In the case of screening for organism-differentiating regions of a human genome, the second organism may be a higher primate.

In some applications of the present invention an identity index, such as percentage of similarity, in a plurality of sub-regions of the nucleic acid sequences are calculated. Sub-regions are overlapping, moving "windows" of base pairs of sequence across the longer sequence. The size of the windows may be adjusted or may be varied, depending on the relatedness of the organisms being compared. Preferably, the window is at least 20 base pairs in length and can be up to 150 base pairs in length, with overlapping bases of 5 to 75 bases for each window. In one embodiment of the present invention, windows of 30 base pairs with 10 base pairs overlap between each window were used. Determining whether the sequence identity between the first and second sequences is high enough to indicate a functional region requires setting a threshold or significance value for sequence identity (percentage of bases that are identical between the two organisms within said sub-region). In practice, a useful selection of this threshold can be done fairly easily and is done commonly. Significance values will differ depending on the relatedness between the organisms, and will be higher the more closely related the organisms.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 2 shows a chromosome 21 reference sequence tiled as 25-mer oligonucleotides (probes). Each nucleotide of the reference sequence was interrogated by four probes-one probe complementary to the sequence and three probes non-complementary to the sequence at the central position (the interrogation position). When the fluorescence intensities (white squares) of the complementary probes are greater than that of the non-complementary probes, similarities between the tiled human sequences and the hybridized animal DNA exist.

The conserved sequence with high conformance (97%) shows the 29 conforming nucleotides. The conserved sequence with low conformance (60%) of 18 conforming nucleotides is also shown.

Figure 4:
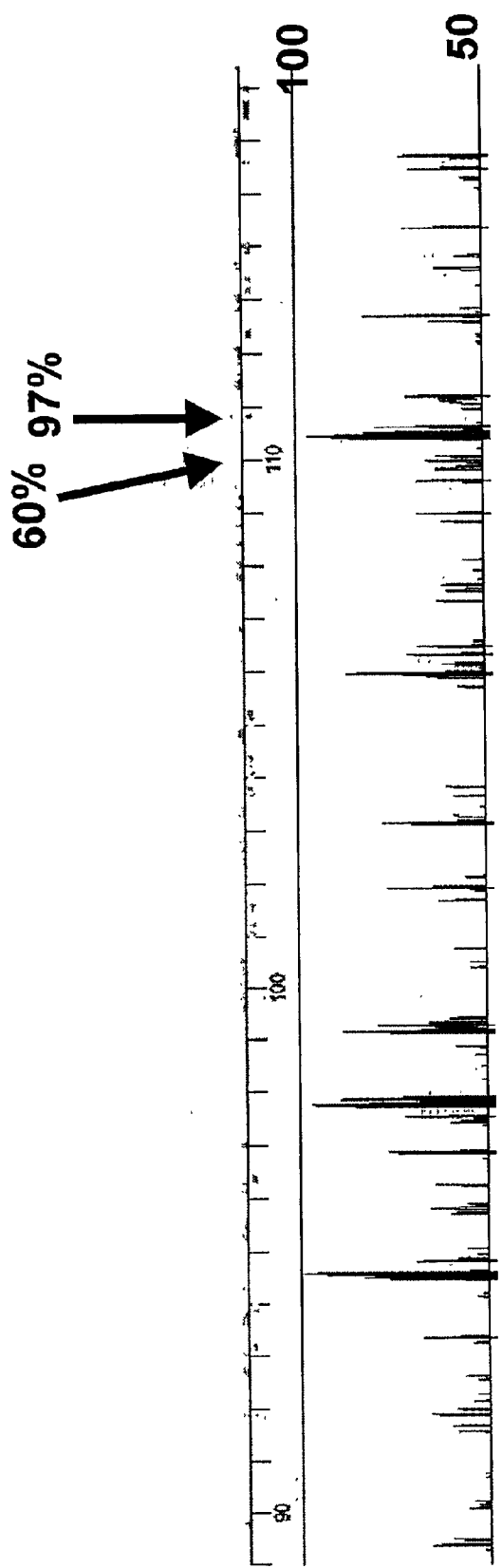

FIG. 4 shows a CONSEQ plot of conserved regions identified by hybridization with syntenic dog sequences for a 26-kb interval on chromosome 21. Conserved elements (highlighted peaks) detected are shown relative to their position in the human reference sequence horizontal axis), and their percent conformance (50–100%) is indicated on the vertical axis. The high conformance (97%) conserved sequence has been merged with neighboring conserved sequences to form a 200-nt conserved element. The low conformance (60%) conserved sequence is a 30-nt element. Small rectangles on the top line indicate the positions of interspersed repeats, which were not tiled on the arrays, therefore conformance information is absent.

Figure 5:
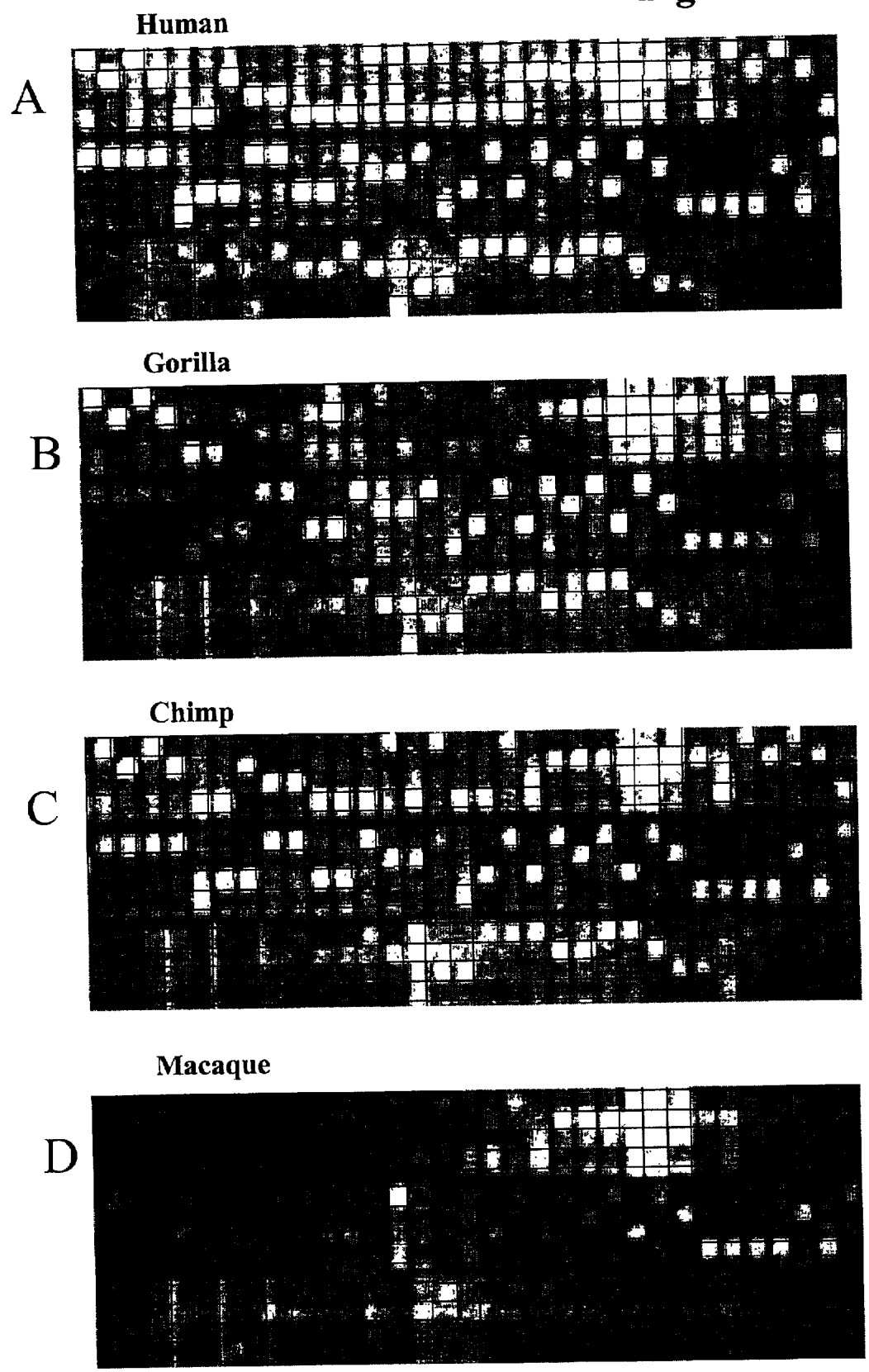

FIG. 5 shows scans of four identical substrate-bound oligonucleotide arrays with probes based on the human genomic sequence from chromosome 21 hybridized with (A) human, (B) gorilla, (C) chimpanzee and (D) macaque genomic DNA samples.

Figure 6:
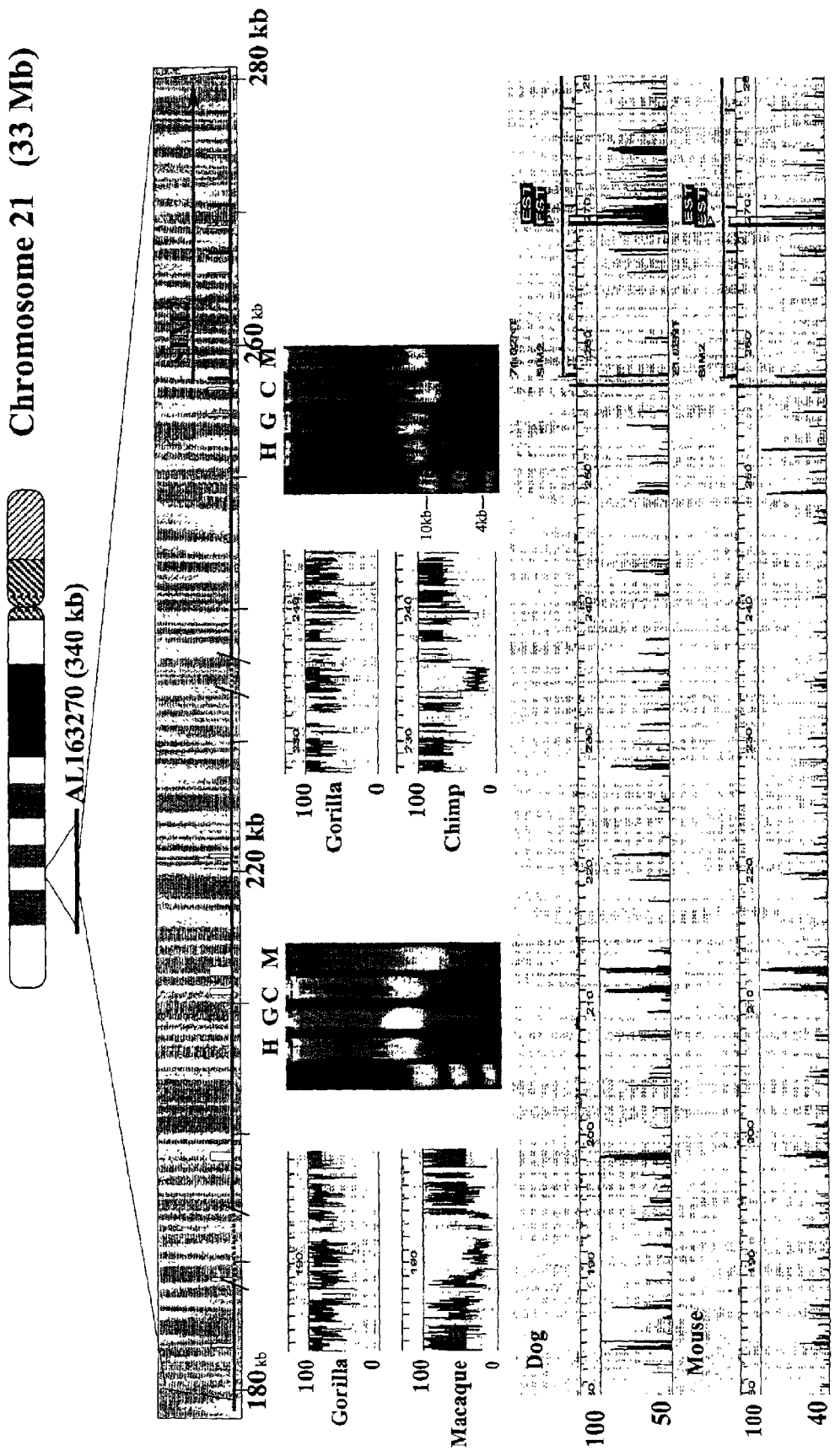

FIG. 6 shows CONSEQ plots of conserved regions identified by hybridization with orthologous dog and mouse sequences for a 100-kb interval on chromosome 21 (bottom two plots). The annotations in these plots are the same as described for FIG. 3. Note that the baseline for sequence similarity in the plot for dog is set at 50% and for mouse is set at 40%. In addition to the dog and mouse plots, CONSEQ plots of conserved regions identified by hybridization with amplified gorilla, macaque and chimp sequences for the >10 kb intervals indicated are shown. In these primate plots, the baseline for sequence similarity is set at 0%. Photographs of the agarose gels of the genomic DNA amplified each primate from the region indicated are also shown.

Figure 7:
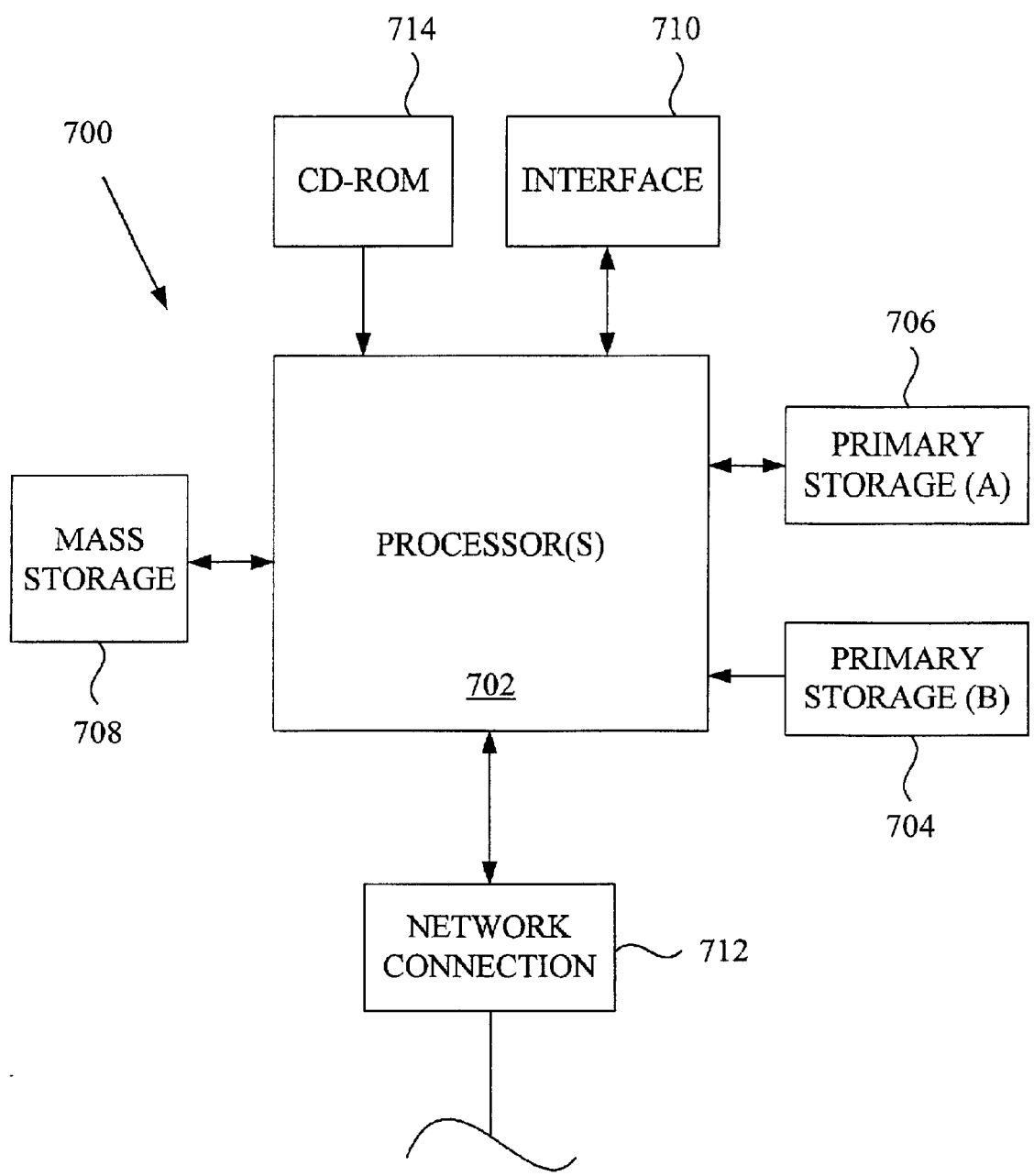

FIG. 7 is a block diagram of a computer system that may be used to implement various aspects of this invention such as the various algorithms for calculating an identity index.

DETAILED DESCRIPTION OF EXAMPLE EMBODIMENTS

Reference will now be made in detail to the preferred embodiments of the invention. While the invention will be described in conjunction with preferred embodiments, it should be understood that such embodiments are not intended to limit the invention to these embodiments. On the contrary, the invention is intended to cover alternatives, modifications and equivalents which are included within the spirit and scope of the invention. For example, the invention will be described by referring to embodiments providing methods, compositions, data analysis systems and computer program products for discovering functional regions in a genome. However, the methods, compositions, computational analysis and computer program products may be useful for analyzing the sequences of other biological molecules, particularly those useful for comparing sequences when one sequence is known and the other is not. In addition, one skilled in the art recognizes that the term "species" is an artificial designation for organisms, and that the present invention can be applied to make sequence comparisons of organisms that are in the same species but in different strains, organisms that are hybrids, or organisms that are related to each other genetically in other ways. Further, although human sequence is used as an example of a reference or known sequence useful in the present invention, the present invention should not be limited to use with human sequence. The reference or known sequence can be any known sequence from any organism.

As used herein the specification, "a" or "an" may mean one or more. As used herein in the claim(s), when used in conjunction with the word "comprising", the words "a" or "an" may mean one or more than one. As used herein "another" may mean at least a second or more.

One skilled in the art recognizes that when first substrate and second substrate are referenced herein that both the first and second substrates could be different substrates or that a single substrate is used in both cases. In the later case, after use of the substrate as the first substrate, the conditions on the substrate are changed such that the sequences hybridized on the first use are removed and the substrate is then used as the second substrate.

All patents and publications mentioned in the specification are indicative of the level of those skilled in the art to which the invention pertains. All patents and publications are herein incorporated by reference to the same extent as if each individual publication was specifically and individually indicated to be incorporated by reference.

A. The Present Invention

The present invention provides biological and computational methods for identifying regions in sequences of an organism that have been conserved through the evolution of that organism. In the methods of the present invention, the nucleic acid sequence of one organism is compared to the nucleic acid sequence of another organism to identify nucleic acid sequence similarities between the organisms.

It has been determined that organisms that diverged evolutionarily over about 120 million years ago share genomic similarity in exonic regions, organisms that diverged evolutionarily between about 60 and about 120 million year ago share genomic similarity in both exonic regions and regulatory elements, and organisms that diverged less than about 60 million years ago share genomic sequence similarity in genomic regions other than exonic regions and regulatory elements. Thus, regions of sequence similarity are more or less informative depending on the relatedness of the two organisms compared. For example, if two organisms diverged evolutionarily between about 60 million and about 120 million years ago, identifying sequences conserved between the organisms would identify putative functional regions (coding and non-coding functional regions) in the genomes of the organisms. As used herein "putative functional regions" includes known functional and also regions that meet the criteria described herein for functional regions but which need further verification or testing to demonstrate they are functional regions. On the other hand, if two organisms diverged evolutionarily less than about 60 million years ago, many sequences may be conserved due to insufficient divergence time. Thus, identifying sequences that are not conserved between the organisms—regions of sequence divergence—would identify putative organism-differentiating and rapidly evolving regions.

First, methods are provided for determining sequence similarity between nucleic acids from a first organism and nucleic acids from a second, different organism without knowing a nucleic acid sequence from the second, different organism. In one application of the present invention, the first nucleic acid is derived from a human, and the second nucleic acid is derived from another animal species. Use of human sequence at this time makes sense as it is one of the few complete genomes that has been sequenced to date; however, the first nucleic acid can be from any organism where the sequence of the nucleic acid is known and the second nucleic acid can be from any organism. The method involves determining which bases from the second nucleic acid are identical to the first nucleic acid, and allows one to determine the sequence of portions of the second nucleic acid.

In a specific embodiments of the invention there is a method for determining sequence similarity between nucleic acids from a first organism and a second organism, comprising the steps of: providing a substrate having a plurality of detection probes, wherein each detection probe is at a known location, and wherein at least one of said detection probes is complementary to a known nucleic acid sequence from said first organism and at least one of said detection probes is non-complementary to a known nucleic acid sequence from said first organism; contacting at least one sample nucleic acid from said second organism with said substrate under conditions wherein when said at least one sample nucleic acid is substantially complementary to a detection probe said at least one sample nucleic acid will preferentially hybidrize to a detection probe to which it is most complementary resulting in at least one hybridized detection probe; determining a location of said at least one hybridized detection probe; and identifying sequences of said at least one hybridized detection probe by referring to the location of said at least one hybridized detection probe; wherein when said sequence of said at least one hybridized detection probe is the same as a sequence complementary to said known nucleic acid sequence from said first organism, there is sequence similarity between nucleic acids from said first organism and said second organism.

Second, methods are provided to screening for functional regions of a first genome from a first organism, by comparing the genomic sequence from the first organism with the genomic sequence of a second organism without knowing a nucleic acid sequence from the second organism. In one application of this method, the first organism is a human, and the second species is a non-human mammal where there is greater than about 60 million years and less than about 120 million years of evolutionary divergence between the human and the non-human mammal. However, the present invention provides that the first organism can be any organism where a sequence of DNA is known and the second organism can be any other organism where there is greater than about 60 million years and less than about 120 million years of evolutionary divergence between the first organism and the second organism. The method involves determining which bases from the nucleic acid from the second species are identical to the bases from the nucleic acid of the first species. Regions where the number of identical bases is above a pre-determined threshold value are regions of putative functional significance in the first species.

Another specific embodiment of the invention includes a method for screening for functional sequences in a genome of a first organism, comprising the steps of: providing a substrate having a plurality of detection probes, wherein each detection probe is at a known location, and wherein at least one of said detection probes is complementary to a known nucleic acid sequence in the genome from said first organism and at least one of said detection probes is non-complementary to a known nucleic acid sequence in the genome from said first organism; contacting at least one sample nucleic acid from a second organism with said substrate, where said second organism diverged evolutionarily from said first organism between about 60 million years ago and about 120 million years ago, and where said contacting is performed under conditions wherein when said at least one sample nucleic acid is substantially complementary to a detection probe said at least one sample nucleic acid will preferentially hybidrize to a detection probe to which it is most complementary, resulting in at least one hybridized detection probe; determining a location of said at least one hybridized detection probe; and identifying sequences of said at least one hybridized detection probe by referring to the location of said at least one hybridized detection probe; wherein when said sequence of said at least one hybridized detection probe is the same as a sequence complementary to said known nucleic acid sequence from said first organism, there is sequence similarity between nucleic acids from said first organism and said second organism, and regions in said nucleic acids of said first organism where there is sequence similarity with said nucleic acids from said second organism are candidate functional regions in said nucleic acids of said first organism.

Third, the invention further provides enhanced methods for analysis of functional regions of a genome. Such methods entail determining regions of a genome that are conserved between a plurality of organisms. Sequences that tend to be conserved between a plurality of organisms are likely to be conserved due to functionality of the sequence, and not be conserved due to chance or insufficient divergence time. Thus, one aspect of the present invention provides methods for identifying actively conserved sequences in the genome of a first organism, as it can be used to compare sequences between a first organism (where the nucleic acid sequence is known) and a second organism (where the nucleic acid sequence is not known), and then between the first organism and a third organism (where the nucleic acid sequence is not known), where there is greater than about 60 million years and less than about 120 million years of evolutionary divergence between the first organism and at least one of the other organisms. Sequences that tend to be conserved between all three organisms are likely to be conserved due to functionality of the sequence, and not be conserved due to insufficient divergence time. Accordingly, comparisons can be done between any number of organisms to achieve greater accuracy. In addition, if one of the other organisms has greater than 60 million years of evolutionary divergence from the first organism, and a third organism has less than 60 million years of evolutionary divergence from the first organism, it is possible to detect sequences which are being conserved and sequences that are evolving rapidly. Sequences that are evolving rapidly have greater than average sequence divergence between one organism and the other and are difficult to detect, i.e., less sequence similarity; but what is similar is important. Yet these rapidly evolving sequences are scientifically and practically very interesting.

Additional specific embodiments of the invention include a method for screening for functional sequences in nucleic acids of a first organism, comprising the steps of: providing a first substrate having a plurality of detection probes, wherein each detection probe is at a known location, and wherein at least one of said detection probes is complementary to a known nucleic acid sequence from said first organism and at least one of said detection probes is non-complementary to a known nucleic acid sequence from said first organism; contacting at least one sample nucleic acid from a second organism with said first substrate under conditions wherein when said at least one sample nucleic acid is substantially complementary to a detection probe said at least one sample nucleic acid will preferentially hybidrize to a detection probe to which it is most complementary, resulting in at least one hybridized detection probe; determining a location of said at least one hybridized detection probe; and identifying sequences of said at least one hybridized detection probe by referring to the location of said at least one hybridized detection probe; wherein when said sequences of said at least one hybridized detection probe is the same as a sequence complementary to said known nucleic acid sequence from said first organism, there is sequence similarity between nucleic acids from said first organism and said second organism; providing a second substrate having a plurality of detection probes, wherein each detection probe is at a known location, and wherein at least one of said detection probes is complementary to a known nucleic acid sequence from said first organism and at least one of said detection probes is non-complementary to a known nucleic acid sequence from said first organism; contacting at least one sample nucleic acid from a third organism with said second substrate under conditions wherein when said at least one sample nucleic acid of said third organism is substantially complementary to a detection probe said at least one sample nucleic acid will preferentially hybidrize to a detection probe to which it is most complementary, resulting in at least one hybridized detection probe; determining a location of said at least one hybridized detection probe; identifying sequences of said at least one hybridized detection probe by referring to the location of said at least one hybridized detection probe; wherein when said sequence of said at least one hybridized detection probe is the same as a sequence complementary to said known nucleic acid sequence from said first organism, there is sequence similarity between nucleic acids from said first organism and said third organism; and identifying regions in said genome of said first organism where there is sequence similarity both with said nucleic acids from said second organism and said nucleic acids from said third organism, wherein said first organism and at least one of said second organism and said third organism diverged evolutionarily between about 60 million years ago and about 120 million years ago, and wherein regions in said nucleic acids from said first organism where there is sequence similarity with both said nucleic acids from said second organism and said third organism are candidate functional regions in said nucleic acid of said first organism.

Fourth, methods are provided to screening for organism-differentiating regions of two organisms by comparing the genomic sequence from a first organism with the genomic sequence of a second organism without having to know the nucleic acid sequence from the second organism, where there is less than about 60 million years of evolutionary divergence between the first organism and the second organism. In one application, the first organism is a human, and the second organism is a gorilla; however, the present invention provides that the first organism can be any organism where a sequence of DNA is known and the second organism can be any other closely-related organism. The method involves determining which bases from the nucleic acid from the second organism are identical to the bases from the nucleic acid of the first organism. The regions where the sequence diverges between the two organisms— i.e., the sequence similarity is below a pre-determined threshold value—are regions of putative organism-differentiating regions in both organisms. In the same way, the present invention allows for one to determine relative relatedness between organisms by using sequence comparison, where the sequence of only one organism needs to be known. A "putative organism-differentiating region" is used to designate regions which are known organism-differentiating regions and those which match the criteria specified herein for organism-differentiating regions, but which need further testing to confirm or verify. The screening tests used herein will identify organism-differentiating regions and putative organism differentiating regions for further study.

A further specific embodiment of the invention is a method for screening for organism-differentiating sequences in nucleic acids of a first organism, comprising the steps of: providing a substrate having a plurality of detection probes, wherein each detection probe is at a known location, and wherein at least one of said detection probes is complementary to a known nucleic acid sequence from said first organism and at least one of said detection probes is non-complementary to a known nucleic acid sequence from said first organism; contacting at least one sample nucleic acid from a second organism with said substrate, where said second organism diverged evolutionarily from said first organism less than about 60 million years ago, and where said contacting is performed under conditions wherein when said at least one sample nucleic acid is substantially complementary to a detection probe said at least one sample nucleic acid will preferentially hybidrize to a detection probe to which it is most complementary, resulting in at least one hybridized detection probe; determining a location of said at least one hybridized detection probe; and identifying sequences of said at least one hybridized detection probe by referring to the location of said at least one hybridized detection probe; wherein when said sequence of said at least one hybridized detection probe is the same as a sequence complementary to said known nucleic acid sequence from said first organism, there is sequence similarity between nucleic acids from said first organism and said second organism, and regions in said nucleic acids of said first organism where there is sequence divergence with said nucleic acids from said second organism are candidate organism-differentiating sequences in said nucleic acids of said first and second organisms.

The present invention also allows one to determine the sequence of genomic regions of an organism where the sequence of these regions was previously unknown. If the sequence of the genome of the first organism is known and the second organism is not, it is possible to determine the sequence of the second organism's genome in regions where the two organisms have sequence similarity. In comparisons between less related organisms, fewer portions of the unknown sequence will be determined. However, comparisons between closely related organisms allow for a large amount of sequence to be determined in the second organism, and this sequence determination can be performed very rapidly.

In a further specific embodiments of the invention there is a method for determining a sequence of nucleic acids from a second organism, comprising the steps of: providing a substrate having a plurality of detection probes, wherein each detection probe is at a known location, and wherein at least one of said detection probes is complementary to a known nucleic acid sequence from a first organism and at least one of said detection probes is non-complementary to a known nucleic acid sequence from said first organism; contacting at least one sample nucleic acid from said second organism with said substrate under conditions wherein when said at least one sample nucleic acid is substantially complementary to a detection probe said at least one sample nucleic acid will preferentially hybidrize to a detection probe to which it is most complementary, resulting in at least one hybridized detection probe; determining a location of said at least one hybridized detection probe; and identifying sequences of said at least one hybridized detection probe by referring to the location of said at least one hybridized detection probe; wherein said sequence of nucleic acids from said second organism can be determined by it being complementary to the sequence of the detection probe.

Further, the invention also provides computational methods and computer software products are provided for sequence comparison between organisms. Such computational methods and computer software products may involve computer software that receives a plurality of hybridization signal intensities from a hybridized array from a detector. The hybridization signal intensities reflect the amount of hybridization of the nucleic acid sample (derived from the second organism) to the detection probes (derived from the sequence of the first organism). Further, such computational methods and computer software may also produce and include, respectively, software modules that identify bases of the sequence of the second organism according to the hybridization intensities. In addition, such computational methods and computer software products may produce and include modules that calculate an identity index between the sequence of the first organism (the detection probe sequence) and the sequence of the second organism (the sample). In one application of the present invention, the identity index is calculated using hidden Markov model predictions. In some applications, the computational methods and computer software produce and include, respectively, functionality that allows an operator to select window size, used to calculate the identity index, and a threshold value. When the identity index of a region is above the threshold value, a putative functional region of the genome is identified.

The present invention also can be used to identify important polymorphisms and single nucleotide polymorphisms. The genomes of humans and other multicellular organisms contain a vast repository of intra-species polymorphic sites of which only a small proportion has functional significance. Some polymorphisms may lack functional significance because they occur within regions of the genome that themselves lack functional significance (e.g., certain intergenic regions). Other polymorphisms may occur in regions of the genome with functional significance; however, these polymorphisms do not affect a resulting amino acid sequence, change an amino acid sequence in a manner that has phenotypic effect, or are silent in non-coding regions with functional significance. The present invention provides methods for narrowing down the total repository of polymorphisms that need be analyzed for functionality, allowing one to focus on the smaller population of polymorphisms that are more likely to have phenotypic effects. The smaller population of polynucleotides are those occupying conserved regions between organisms.

In another specific embodiment of the invention there is a method for screening for genomic regions where polymorphisms have phenotypic effect in a first organism, comprising the steps of: providing a substrate having a plurality of detection probes, wherein each detection probe is at a known location, and wherein at least one of said detection probes is complementary to a known nucleic acid sequence from said first organism and at least one of said detection probes is non-complementary to a known nucleic acid sequence from said first organism; contacting at least one sample nucleic acid from a second organism with said substrate, where said second organism diverged evolutionarily from said first organism between about 60 million years ago and about 120 million years ago, and where said contacting is performed under conditions wherein when said at least one sample nucleic acid is substantially complementary to a detection probe said at least one sample nucleic acid will preferentially hybidrize to a detection probe to which it is most complementary, resulting in at least one hybridized detection probe; determining a location of said at least one hybridized detection probe; and identifying sequences of said at least one hybridized detection probe by referring to the location of said at least one hybridized detection probe; wherein when said sequence of said at least one hybridized detection probe is the same as a sequence complementary to said known nucleic acid sequence from said first organism, there is sequence similarity between nucleic acids from said first organism and said second organism, and regions in said nucleic acids of said first organism where there is sequence similarity with said nucleic acids from said second organism are regions where polymorphisms have phenotypic effect in a first organism.

In the present invention, hybridization is performed between a plurality of detection probes designed to be complementary and one-base mismatch non-complementary to genomic sequence derived from one organism (the reference sequence). The detection probes use, for example, the first organism's genomic sequence as a reference sequence and genomic DNA extracted from the second organism is used to produce the nucleic acid sample (or target nucleic acid). The genomic sequences of the first and second organisms are compared by evaluating the amount and position of hybridization that takes place between the detection probes and the nucleic acid sample.

In any of the specific embodiments one skilled in the art recognizes that any nucleic acid which is known in at least one organism can be used. In one preferred embodiment genomic DNA is used.

The plurality of probes can be at any a density that is useful to practice the invention. Substrates with a plurality of probes are known in the art. In specific preferred embodiments the density is at least 100 probes/cm$^2$; or is at least 1,000 probes/cm$^2$; or is at least 10,000 probes/cm$^2$.

In practicing the invention one skilled in the art knows how to determine the best length of probe to further hybridization. In preferred embodiments of the present invention the probes are at least 18 bases long or are at least 20 bases long or are at least 25 bases long.

One skilled in the art recognizes that any of the preferred embodiments can include an additional step of calculating an identity index between sub-regions of the nucleic acids from a first organism and the nucleic acids from a second organism. Generally the identity index is calculated by determining a percentage of similarity between sub-regions of said nucleic acids from the first organism and the nucleic acids from said second organism.

B. General Methods and Protocols

1. Array Design

Comparative sequence analysis was performed using immobilized nucleic acid probes. Methods for designing, selecting and making probe sets are described in, for example, WO 95/11995, WO 92/10092, or U.S. Pat. Nos. 5,143,854; 5,384,261; 5,405,783; 5,412,087; 5,424,186; 5,445,934; 5,744,305; 5,800,992; 6,040,138; 6,040,193, all of which are incorporated herein by reference for all purposes. One with skill in the art would appreciate that the detection arrays of the present invention are not limited to one particular manufacturing method. For example, oligonucleotide probes may be pre-synthesized and deposited on a substrate. Detection, as used herein, refers to processes including identifying base composition and sequence of a target sequence based upon the known sequence of a reference nucleic acid. The detection probe arrays or chips are designed using this reference sequence, typically the genomic sequence of a first organism.

The basic strategy for array design provides an array that is subdivided into sets of four probes (oligonucleotides of differing sequence), although in some situations, more or less probes per set may be appropriate. In a typical embodiment, one probe in each probe set comprises a plurality of bases exhibiting perfect complementarity with a selected reference sequence (i.e., the genomic sequence of a first species). In this probe of the set, complementarity with the reference sequence exists throughout the length of the probe. For the other three probes in the set, complementarity with the reference sequence exists throughout the length of the probe except for an interrogation position, which typically consists of one nucleotide base at or near the center of probe. For example, for an A nucleotide in the reference sequence, the corresponding probe with perfect complementarity from the probe set has its interrogation position occupied by a T, the correct complementary base. The other probes from the set have their respective interrogation positions occupied by A, C, or G—a different nucleotide in each probe. Thus, there are four probes corresponding to each nucleotide of interest in the reference sequence. Alternative embodiments exist, however, and the present invention should not be limited to arrays with four probes per probe set. A five-probe per set embodiment is described infra.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phosphodiester bonds. The probes can be attached by any linkage to a support (e.g., 3', 5' or via the base). Attachment at the 3' end of the probe is usual as this orientation is compatible with the preferred chemistry for solid phase synthesis of oligonucleotides.

For simplicity, the sets are usually arranged in order of the reference sequence in a horizontal row across the array, though other embodiments are used. A horizontal row contains a series of overlapping probes with the same base at the interrogation position. These overlapping probes span the selected reference sequence. Each set of four probes usually differs from the previous set of four probes by the omission of a base at one end and the inclusion of an additional base at the other end. However, this orderly progression of probes may be interrupted by the inclusion of control probes or the omission of certain probes in rows or columns of the array. In addition, probes may be placed so as to orient the array, or gauge the background or non-specific binding of the sample to the array. One of skill in the art would appreciate that the probes may not be necessarily arranged in such an order as described above, but could be in any order as long as the sequence of a probe can be correlated to location on the array.

The sets of probes are usually laid down in horizontal rows such that all probes having an interrogation position occupied by an A form an "A row" in the vertical direction, all probes having an interrogation position occupied by a C form a "C row", all probes having an interrogation position occupied by a G form a "G row", and all probes having an interrogation position occupied by a T (or U) form a T row (or a U row).

In most arrays, all probes are the same length. Optimum probe length may vary depending on, among other things, the GC content of a particular region of the target DNA sequence, secondary structure, synthesis efficiency and cross-hybridization. The appropriate size of probes at different regions of the target sequence can be determined by comparing the readability of different sized probes in different regions of a target.

In preferred embodiments of the present invention, the arrays are designed to have sets of probes complementary to both strands of the reference sequence (coding or non-coding). Independent analysis of coding and non-coding strands provides largely redundant information; however, the regions of ambiguity in reading the coding strand are not always the same as those in reading the non-coding strand. Thus, combination of the information from coding and non-coding strands increases the overall accuracy of the sequence data.

Figure 1:
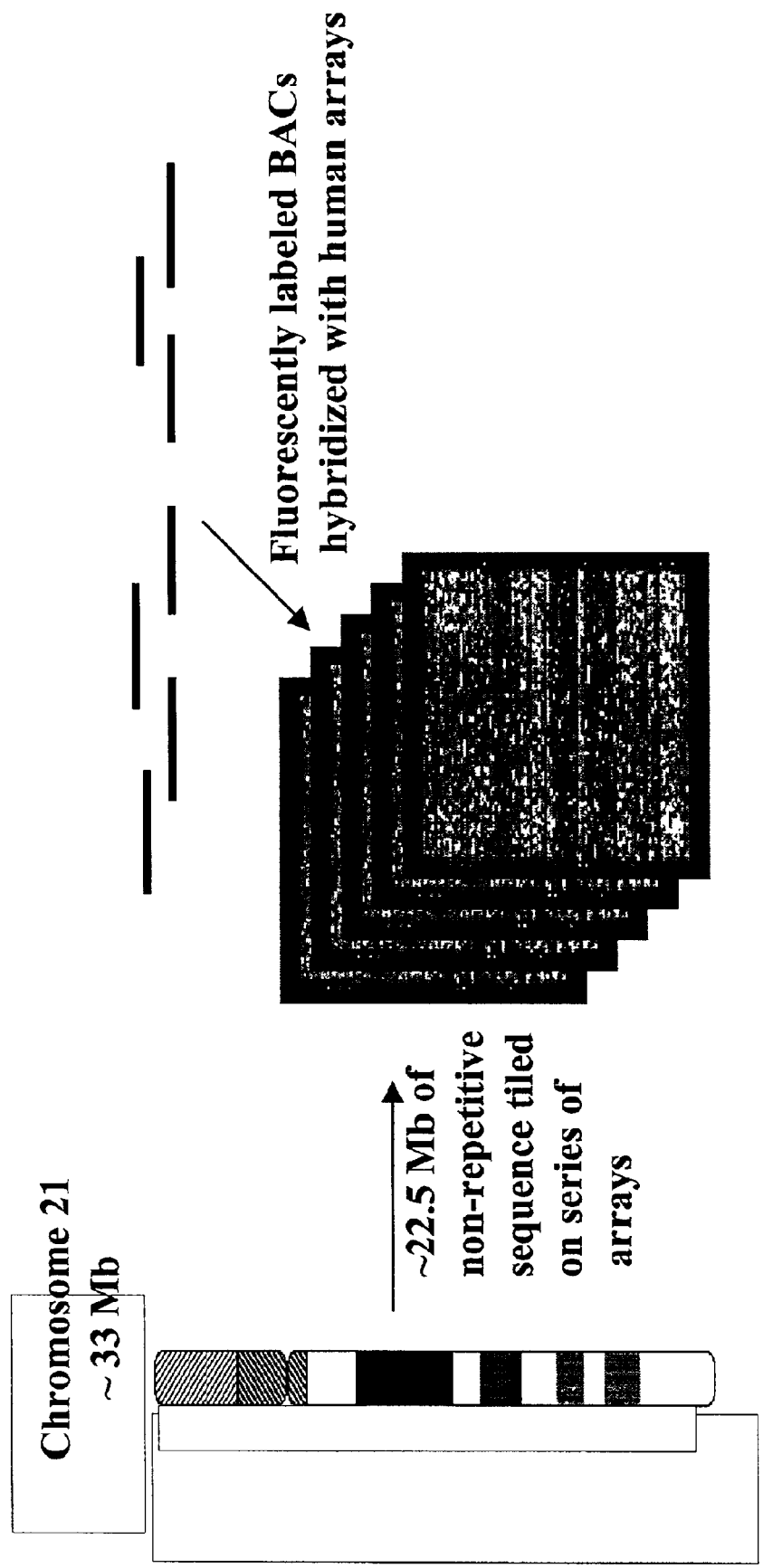
FIG. 1 is a schematic of the detection and analysis of evolutionarily conserved sequences on human chromosome 21. The chromosome 21 arrays were designed using non-repetitive sequences and hybridized with syntenic mouse and dog BACs that are represented as horizontal lines. A low magnification view of fluorescence hybridization image of an array is shown.
Figure 3:
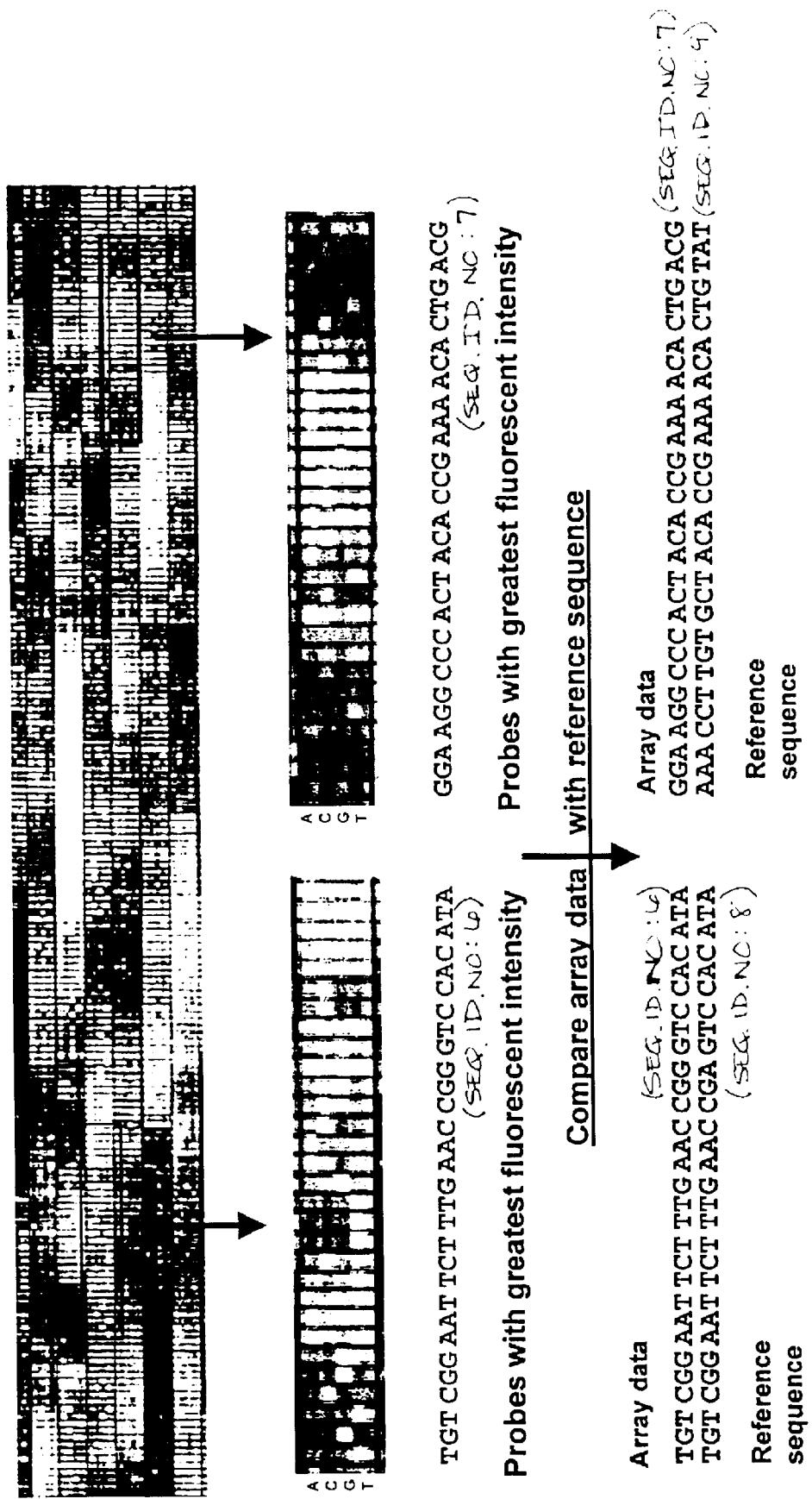
FIG. 3 shows an enlarged view of a human 21 q array hybridized with syntenic dog BAC DNA (top). Two 30 nucleotide intervals, one with high conformance between the human and dog sequences (left rectangle in array display) and one with low conformance between human and dog sequences (right rectangle in array display), are shown.

The arrays are read by comparing the intensities of labeled target nucleotides (amplified genomic DNA from the second species) that are bound to the probes (oligonucleotides engineered to be complementary to the sequence of genomic DNA of a first species) on an array after hybridization (in general, see FIGS. 1–3). Specifically, a comparison is performed between each probe (e.g., probes differing in their interrogation position by an A, C, G and T) of each probe set. For a particular probe set, the probe position showing the greatest hybridization signal is called as the nucleotide present at the position in the target sequence corresponding to the interrogation position in the probes. Clearly, of the four probes in a set, only one can exhibit, for example, a perfect match to the target sequence whereas the other probes of the set exhibit at least a one base pair mismatch. However, in some regions of the target sequence, the distinction between a perfect match and a one-base mismatch is less clear, or, frequently, there may be more than one mismatched base, in which case one probe will have, instead of perfect complementarity, one base greater complementarity than the other probes of the set. The probe exhibiting the best match usually produces substantially greater hybridization signal than the other three probes in the column and is thereby easily identified. In one embodiment of the present invention, the probe with the best hybridization signal is called as the sequence nucleotide. In other embodiments of the present invention, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read. A lower call ratio results in fewer ambiguous calls, but can result in more erroneous calls. It has been found that at a call ratio of 1.2, virtually all calls are accurate.

For target sequences showing a high degree of divergence from the reference strain or incorporating several closely spaced mutations from the reference strain, a single set of probes (i.e., designed with respect to a single reference sequence) will not always allow accurate sequence to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read. The presence of short regions of difficult-to-read target because of closely spaced mutations, insertions or deletions, does not prevent determination of the remaining sequence of the target as different regions of a target sequence are determined independently.

When the arrays comprise four-probe sets, and the probe sets are laid down in columns to form rows—an A row, a C row, a G row and a T or U row—the probe having a segment exhibiting perfect complementarity to a reference sequence varies between the columns from one row to another. This does not present any significant difficulty in computer analysis of the data from the array. However, visual inspection of the hybridization pattern of the array is sometimes facilitated by provision of an extra probe (a fifth probe in each set), which exhibits perfect complementarity to the reference sequence. This fifth probe is identical to one of the other probes of the set. The extra probes may be placed to form a row (designated the wildtype row) and would hybridize to a target sequence at all nucleotide positions except those in which deviations from the reference sequence occurs. The hybridization pattern of the wildtype row thereby provides a simple visual indication of sequence similarity and dissimilarity.

2. Preparation of the Nucleic Acid Target

The target polynucleotide, whose sequence is to be determined, is usually isolated from a tissue sample from the organism of interest. If the target is genomic DNA, the sample may be from any tissue (except red blood cells). These sources are also suitable if the target is RNA. Methods for isolating genomic DNA are known in the art (see, e.g., Sambrook, et al., *Molecular Cloning: A Laboratory Manual* (1989), 2d Ed., Cold Spring Harbor, N.Y.).

In certain embodiments of the present invention, the DNA for the nucleic acid sample is amplified. Amplification methods are well known in the art, and the method selected generally depends on the size of the regions to be amplified. If, for example, the regions to be amplified are contained in vectors or artificial chromosomes, PCR methods known in the art can be employed. If the DNA to be amplified is genomic DNA, long range PCR methods preferentially are employed. In order to amplify genomic DNA, PCR primers must be designed for the amplification reaction. Primers used for the amplification reaction are designed in the following way: a given sequence, usually the reference sequence, is fed in to a software program called "Repeat Masker" which recognizes sequences that am repeated in the genome (e.g., Alu and Line elements) (A. F. A. Smit and P. Green, www.genome.washington.edu/uwgc/analysistools/repeatmask.htm). The repeated sequences are "masked" by the program by substituting the specific nucleotides of the sequence (A, T, G or C) with "Ns". The sequence output after the repeat mask substitution can then be analyzed by a commercially available primer design program (for example, Oligo 6.23 or PrimerSelect) to select primers that meet criteria appropriate for the size of the regions to be amplified and the reaction conditions chosen. For example, primer criteria used might dictate that the primers have a length of greater than 30 nucleotides, melting temperatures of over 65° C., and amplify at least 3,000 bps of the genome. In a preferred embodiment, each primer pair is tested by performing two PCR reactions, one with genomic DNA matching the reference sequence (that is, nucleic acid isolated from the first species) and the other with target DNA. This test is performed to determine whether the primer pair produces a single clear amplified fragment visible by agarose gel electrophoresis and ethidium bromide staining.

PCR reactions may be performed by methods known in the art. Such methods are described in laboratory manuals such as Sambrook, et al., *Molecular Cloning: A Laboratory Manual* (1989), 2d Ed., Cold Spring Harbor, N.Y. Long distance PCR is described in, for example, product literature from, e.g., Roche (Expand Long Template PCR System), or Talcara Shuzo Co., Ltd. (TaKaRa LA Taq), as described in U.S. Pat. No. 5,512,462 to Cheung, or as described in U.S. Ser. No. 60/213,186, all of which are incorporated in their entirety herein by reference. In addition, more than one target region can be amplified simultaneously by multiplex PCR in which multiple paired primers are used in a single amplification reaction. The target can be labeled at one or more nucleotides during or after amplification. Many labels are known in the art, including luminescent labels, radioactive labels, and light scattering labels. Preferably, the label is a luminescent label, such as fluorescent, chemiluminescent, bioluminescent or calorimetric labels. The target preferably is fragmented before hybridization with the array to reduce or eliminate the formation of secondary structures in the target. The average size of target segments following hybridization is usually larger than the size of probe on the chip.

In one example of the present invention, PCR reactions were performed in a 25-$\mu l$ volume containing 10 ng of genomic DNA or 1 ng of purified BAC DNA, 1 mM of each primer, 2.5 units of AmpliTaq Gold (Perkin-Elmer), 0.25 mM deoxynucleotide triphosphates (dNTPs), 10 mM tris-HCl (pH 8.3), and 50 mM KCl, and 1.25 mM $MgCl_2$. Thermocycling was performed on a 9600 or 9700 automated thermal cycler (Perkin-Elmer), with initial denaturation at 95° C. for 10 min, followed by one of two cycling conditions based on the melting temperature of the primers: either 10 cycles of [94° C. 30 sec, 58° C. 30 sec, 72° C. 30 sec] followed by 30 cycles of [94° C. 30 sec, 55° C. 30 sec, 72° C. 30 sec] or 10 cycles of [94° C. 30 sec, 55° C. 30 sec, 72° C. 30 sec] followed by 30 cycles of [94° C. 30 sec 52° C. 30 sec, 72° C. 30 sec]. A final extension reaction was carried out 72° C. for 5 min. The amplified DNA was then purified using the Qiagen Large-Construct Kit (Qiagen), fragmented with deoxyribonuclease (DNase) 1 (Boehringer Manneheim) and labeled with biotin with terminal deoxynucleotidyl transferase (TdT, GibcoBRL Life Technology). Fragmentation was performed in a 74-$\mu l$ volume with 0.2 unit of DNase 1, 10 mM tris-acetate (pH 7.5), 10 mM magnesium acetate, and 50 mM potassium acetate at 37° C. for 10 min, after which the reaction was stopped by heat inactivation at 99° C. for 10 min. The terminal transferase reaction was performed by adding 50 units of TdT and 12.5 $\mu M$ biotin-N6-ddATP (Dupont NEN) to the preceding reaction mix, incubating at 37° C. for 90 min, and then heat-inactivating at 99° C. for 10 min.

3. Oligonucleotide Array Hybridization

Hybridization assays on a substrate-bound oligonucleotide arrays involve a hybridization step and a detection step. In the hybridization step, a hybridization mixture containing the target and, typically, an isostabilizing agent, denaturing agent or renaturation accelerant, is brought into contact with the probes of the array and incubated at a temperature and for a time appropriate to allow hybridization between the target and any complementary probes. Usually, unbound target molecules are then removed from the array by washing with a wash mixture that does not contain the target, leaving only bound target molecules.

The hybridization mixture includes the target nucleic acid molecule and hybridization optimizing agents in an appropriate solution (buffer). The target nucleic acid is present in the mixture at a concentration between about 0.005 nM target per ml hybridization mixture and about 50 nM target per ml hybridization mixture. The hybridization mixture is placed in contact with the array and incubated. Generally, incubation will be at temperatures normally used for hybridization of nucleic acids, for example, between about 25° C. and 65° C. For probes longer than 14 nucleotides, a temperature range of 37° C. and 45° C. is preferred. Incubation time varies, but can be as short as 30 minutes and as long as 12 hours or more. After incubation with the hybridization mixture, the array is usually washed with buffer. Examples of general hybridization conditions may be found in many sources, including: Sambrook, et al., *Molecular Cloning: A Laboratory Manual* (1989), 2d Ed., Cold Spring Harbor, N.Y.; Berger and Kimmel, "Guide to Molecular Cloning Techniques", *Methods in Enzymology* (1987), Vol. 52, Academic Press, Inc.; Young and Davis, Proc. Natl. Acad. Sci. (USA) 80:1194 (1983). Hybridization conditions specific for oligonucleotide arrays can be found in product literature from Affymetrix, Inc. (Santa Clara, Calif.) and U.S. Pat. No. 6,045,996 to Cronin et al.

In one example of the present invention, DNA labeling and hybridization to arrays was performed as described in D. G. Wang et al., Science 280:1077 (1998), with minor modifications. The labeled DNA sample was denatured in hybridization buffer [3M tetramethylammonium chloride, 10 mM tris-HCl (pH7.8), 0.01% Triton X-100, herring sperm DNA (100 µg/ml), and 50 pM control oliogomer] at 99° C. for 5 min and hybridized to an oligonucleotide array overnight at 40° C. on a rotisserie at 40 rpm. All washes and staining were performed at room temperature. Oligonucleotide arrays were washed twice with 1×MES buffer [0.1 M 2-[N-Morpoline]ethanesulfonic acid (pH 6.7), 1 M NaCl, and 0.01% Triton X-100], and stained with staining solution [streptavidin R-phycoerythrin (20 µg/ml) (Molecular Probes) and acetylated bovine serum albumin (BSA) (1 mg/ml) in 2×MES] for 20 min on a rotisserie at 40 rpm. Following two washes with 1×MES, chips were incubated with antibody solution [biotinylated anti-streptavidin antibody (10 µg/ml) and BSA (1 mg/ml) in 2×MES] for 20 min on a rotisserie at 40 rpm. After two washes with 1×MES, arrays were stained again with staining solution for 20 min. The oligonucleotide arrays were washed 6 times with 6×SSPET [0.9 M NaCl, 60 mM $NaH_2PO_4$, 6 mM EDTA (pH7.4), 0.01% Triton X-100] at 35° C. on a fluidics workstation (Affymetrix).

Determining a signal generated from a detectable label on an array requires an oligonucleotide array or chip reader. The nature of the oligonucleotide array reader depends upon the particular type of label attached to the target molecules. A typical reader employs a system where the light source is placed above the array to be scanned and a photodiode detector is below the array. A preferred reader replaces the photodiode with a CCD camera and imaging optics to allow rapid imaging of the array. In one example of the present invention, hybridization of target DNA to the array was detected by using a custom confocal scanner with a resolution of 110 pixels per feature (pixel size of 2.27 µM) and 560-nm filter.

4. Computational Analysis

An identification procedure can be developed by inspecting known sequences from two different organisms, and performing analysis on the sequences. Conformance can be computed over varying sequence lengths or "window sizes". However, the windows must be overlapping to avoid artificial boundaries for calculation of percent similarity. Comparing sequence between, for example, a mouse and a human, it was determined that windows of 30 base pairs with an overlap of 10 base pairs that had conformance of 60% or higher showed strong similarity between human and mouse, except in cases where the window was close to or within a repeat or a region of low complexity. Further, it was determined that windows that were within 20 base pairs of a repeat sometimes showed spuriously high conformance. Likewise, inspection of windows with high conformance led to the decision that windows in which the reference sequence had either (a) 50% or more of a single base (either A, G, T, or C) or (b) 67% or more of a single base within any sub-window of 15 base pairs within the 30-base pair window (i.e., 10 or more out of 15), would sometimes show high conformance. Such sequences of low local complexity were considered not of interest, and were therefore not classified as potentially conserved. Further inspection of sequence similarities led to the conclusion that nearby windows with high conformance were likely to be parts of the same potentially-conserved element. For example, there were clear cases where an exon was conserved and most, but not all, windows covering that exon showed high conformance. Thus, it was determined that regions of 120 base pairs or less between potentially conserved-windows would also be declared as potentially conserved.

Likewise, the procedure for determining potentially conserved-regions may be a multi-step process. The first step may compute conformance for all 30-base pair windows (with 10-base pair overlap). In other words, conformance is computed for base pairs 1–30, 21–50, 41–70, and so on, as the percent of probes matching the reference sequence (of the 60 probes—30 for the Watson strand, 30 for the Crick strand). Next, the distance of each window from the nearest known repeat is computed, masking the repeat regions on the reference sequence. The maximum frequency of any base in the reference sequence corresponding to each window may then be computed, and finally, the maximum frequency of any base within a sub-window of 15 base pairs within the reference sequence may be computed for each window.

After these statistics are computed, windows may be classified as potentially conserved for which (a) conformance is at some percent, (b) nearest repeat is at some distance, (c) maximum single-base frequency is less than some percent, and (d) maximum single-base frequency for any 15-base pair sub-window is less than some percent. Then, for all potentially-conserved windows within so many base pairs of another potentially-conserved window, the windows between them are classified as potentially conserved. Finally, from the collection of potentially-conserved windows, the potentially-conserved contiguous regions were computed.

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

FIG. 7 illustrates a typical computer system that, when appropriately configured or designed, can serve as an image analysis apparatus of this invention. The computer system 700 includes any number of processors 702 (also referred to as central processing units, or CPUs) that are coupled to storage devices including primary storage 706 (typically a random access memory, or RAM), primary storage 704 (typically a read only memory, or ROM). CPU 702 may be of various types including microcontrollers and microprocessors such as programmable devices (e.g., CPLDs and FPGAs) and unprogrammable devices such as gate array ASICs or general purpose microprocessors. As is well known in the art, primary storage 704 acts to transfer data and instructions uni-directionally to the CPU and primary storage 706 is used typically to transfer data and instructions in a bi-directional manner. Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk. It will be appreciated that the information retained within the mass storage device 708, may, in appropriate cases, be incorporated in standard fashion as part of primary storage 706 as virtual memory. A specific mass storage device such as a CD-ROM 714 may also pass data uni-directionally to the CPU.

CPU 702 is also coupled to an interface 710 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 702 optionally may be coupled to an external device such as a database or a computer or telecommunications network using an external connection as shown generally at 712. With such a connection, it is contemplated that the CPU might receive information from the network, or might output information to the network in the course of performing the method steps described herein.

In one embodiment, the computer system 700 is directly coupled to a hybridization detector or scanner. Data from the detector are provided via interface 712 for analysis by system 700. Alternatively, the data or hybridization signal intensities processed by system 700 are provided from a data storage source such as a database or other repository. Again, the data are provided via interface 712. Once in the computer system 700, a memory device such as primary storage 706 or mass storage 708 buffers or stores, at least temporarily, the data or hybridization intensities. With this data, the image analysis apparatus 700 can perform various analysis operations such as calculating intensities indices and the like. To this end, the processor may perform various operations on the stored images or data.

The invention thus also provides for an apparatus for identifying evolutionarily conserved sequences. This apparatus comprises a scanner for scanning hybridization intensities; a first memory region for storing data said hybridization intensities; a second memory region for storing process steps; and a processor for executing the process steps stored in said second memory region; wherein said second memory region includes process steps to (a) receive a plurality of hybridization intensities wherein each of said intensities reflects the hybridization of one of a plurality of probes from a first nucleic acid sequence from a first organism to a sample nucleic acid from a second organism, wherein said probes are complementary and non-complementary to a known nucleic acid sequence from said first organism, wherein said probes are arrayed on a substrate and wherein each detection probe is at a known location on said substrate, (b) identify bases of said plurality of probes according to said hybridization intensities, and (c) calculate an identity index between said first nucleic acid sequence from said first organism and said sample nucleic acid from said second organism. The apparatus optionally further comprises a database including said identity index and hybridization intensities.

Another embodiment of the present invention is drawn to a computer program product comprising a machine readable medium on which is provided program instructions for identifying evolutionarily conserved and/or divergent sequences. The instructions comprises code for receiving a plurality of hybridization intensities wherein each of the intensities reflects the hybridization of one of a plurality of probes from a first nucleic acid sequence from a first organism to a sample nucleic acid from a second organism, wherein the probes are complementary and non-complementary to a known nucleic acid sequence from the first organism, wherein the probes are arrayed on a substrate and wherein each detection probe is at a known location on the substrate; code for identifying bases of the plurality of probes according to the hybridization intensities; and code for calculating an identity index between the first nucleic acid sequence from the first organism and the sample nucleic acid from the second organism. In a further embodiment, the computer program product further comprises code for storing and retrieving hybridization intensities and identity indices.

The invention also provides for a computing device comprising a memory device configured to store at least temporarily program instructions for identifying evolutionarily conserved and/or divergent sequences, the instructions comprising: code for receiving a plurality of hybridization intensities wherein each of the intensities reflects the hybridization of one of a plurality of probes from a first nucleic acid sequence from a first organism to a sample nucleic acid from a second organism, wherein the probes are complementary and non-complementary to a known nucleic acid sequence from the first organism, wherein the probes are arrayed on a substrate and wherein each detection probe is at a known location on the substrate; code for identifying bases of the plurality of probes according to the hybridization intensities; and code for calculating an identity index between the first nucleic acid sequence from the first organism and the sample nucleic acid from the second organism. In a further embodiment, the computing device further comprises code for storing and retrieving hybridization intensities and identity indices.

B. Examples

1. Evolutionarily Conserved Sequences on Human Chromosome 21 by Comparing Human and Dog and Human and Mouse Sequences Chromosome 21 was examined for evolutionarily conserved elements by hybridization of mouse and dog bacteria artificial chromosome (BAC) sequences to human oligonucleotide arrays. For cross-species comparisons, it is important to insure that the sequences are orthologous (derived from the same piece of DNA) and not paralogous (similar due to a duplication of DNA). If paralogous sequences between two species are compared, the number of conserved elements can be underestimated. In this study, mouse and dog BACs were considered orthologous if they contained two or more markers present on human chromosome 21 (comparative anchor tag sequences (CATS)) and formed part of a contig. In addition, BACs identified by a single marker, such as those at the edge of a contig or in a region not spanned by a contig, were considered orthologous if extended regions of conservation outside of known coding sequences were observed when they were hybridized to the oligonucleotide arrays.

Orthologous chromosome 21 sequences were isolated using CATS to coding and non-coding conserved elements. 106 human chromosome 21 segments were obtained through (www.ncbi.nlm.nih.gov/genome/seq/chr.cgi?CHR=21 & SRT=size & MIN=0 & ORG=Hs), masked for repeats using RepeatMasker2 (A. F. A. Smit & P. Green, supra) and queried against the Mouse BAC End (at ftp.tigr.org/pub/data/m_musculus/bac_end_sequences/), GenBank nt and dbEST (restricted to the mouse) databases using BLAST (S. F. Altshul, supra). Matches between chromosome 21 DNA and sequences in the Mouse BAC End (with and B value $\leq 10^{-10}$) and GenBank (to known or suspected mouse orthologs) databases were used to design CATSs (with ~50% GC content and a predicted product of 100–200 basepairs). Each primer pair was individually tested against human and mouse genomic DNA to determine if the pair produced a single clear fragment visible by agarose gel electrophoresis and ethidium-bomide staining. All mouse-specific primers used in the study were obtained from either the Mouse Genome Database (www.informantics.jax.org/) or the WICGOR Mouse RH Map www.genome.wi.mit.edu/mouse_rh/index.html). A total of 123 CATS were developed. These markers along with mouse-specific syntenic markers were used to screen the RPCI-23 mouse BAC library by the polymerase chain reaction (PCR).

PCR reactions were performed in a 25-$\mu$l volume containing 10 ng of genomic DNA or 1 ng of purified BAC DNA, 1 mM of each primer, 2.5 units of AmpliTaq Gold (Perkin-Elmer), 0.25 mM deoxynucleotide triphosphates (dNTPs), 10 mM tris-HCl (pH 8.3), 50 mM KCl, and 1.25 mM $MgCl_2$. Thermocycling was performed on a 9600 or 9700 (Perkin-Elmer), with initial denaturation at 95° C. for 10 min, followed by one of two cycling conditions based on the melting temperature of the primers: either 10 cycles of [94° C. 30 sec, 58° C. 30 sec, 72° C. 30 sec] followed by 30 cycles of [94° C. 30 sec, 55° C. 30 sec, 72° C. 30 sec] or 10 cycles of [94° C. 30 sec, 55° C. 30 sec, 72° C. 30 sec] followed by 30 cycles of [94° C. 30 sec, 52° C. 30 sec, 72° C. 30 sec]. A final extension reaction was carried out at 72° C. for 5 min. To score BACs for the presence or absence of markers, 10-$\mu$l of the PCR amplification product was assayed by 2% agarose gel electrophoresis and ethidium-bromide staining.

These efforts combined with existing mouse maps (see T. Wiltshire, et al., Genome Res. 9:1214 (1999) and M. Pletcher, et al., Genomics, submitted) resulted in the assembly of >360 mouse BACs and plasmid artificial chromosomes (PACs) into 35 contigs which span ~74% of the syntenic human chromosome 21 sequences.

A 6-Mb 21q22 region, known as the Down Syndrome Critical Region, was targeted for human-dog analysis because of the intense biological interest in this interval. Twenty-one CATS spanning the 6-Mb 21q22 interval were amplified from dog genomic DNA by PCR and used to screen the RPCI-65 dog BAC library by hybridization. Sixty-one dog BACs were isolated, characterized by PCR content mapping, and assembled into 9 contigs covering ~4 Mb (67%) of the targeted syntenic chromosome 21 region.

Human chromosome 21 sequence was used to design high-density arrays consisting of 25-mer oligonucleotides (probes) (see, for example, FIGS. 1–3) (for methods, see, for example, M. Chee, et al., Science 274: 610 (1996); S. P. Fodor, et al., 767 (1991); A. C. Pease, et al., Proc. Natl. Acad. Sci. USA 91:5022 (1994)) and WO 95/11995, WO 92/10092, or U.S. Pat. Nos. 5,143,854; 5,384,261; 5,405,783; 5,412,087; 5,424,186; 5,445,934; 5,744,305; 5,800,992; 6,040,138; 6,040,193, all of which are incorporated herein by reference for all purposes). Four probes were designed to interrogate each nucleotide present on each strand of chromosome 21 sequence, one probe complementary to the sequence and three mismatch probes identical to the complementary probe except for the nucleotide at the central position (the $13^{th}$ position) under interrogation. At this central position, each mismatch probe contains one of the bases not identical to the perfect match probe. In this study ~276 arrays containing greater than 130 million oligonucleotides were used to interrogate ~33-Mb of non-repetitive chromosome 21 sequence (~16.5-Mb of each Watson and Crick complementary strands).

DNA labeling and hybridization to arrays was performed as described in D. G. Wang et al., Science 280: 1077 (1998) with minor modifications. 30 $\mu$g of purified BAC DNA was fragmented with deoxyribonuclease (DNase) 1 (Boehringer Manneheim) and labeled with biotin with terminal deoxynucleotidyl transferase (TdT, GibcoBRL Life Technology). Fragmentation was performed in a 74-$\mu$l volume with 0.2 unit of DNase 1, 10 mM tris-acetate (pH 7.5), 10 mM magnesium acetate, and 50 mM potassium acetate at 37° C. for 10 min, after which the reaction was stopped by heat inactivation at 99° C. for 10 min. The terminal transferase reaction was performed by adding 50 units of TdT and 12.5 $\mu$M biotin-N6-ddATP (Dupont NEN) to the preceding reaction mix, incubating at 37° C. for 90 min, and then heat-inactivating at 99° C. for 10 min. Next, labeled DNA sample was denatured in hybridization buffer [3M tetramethylammonium chloride, 10 mM tris-HCl (pH7.8), 0.01% Triton X-100, herring sperm DNA (100 $\mu$g/ml), and 50 pM control oliogomer] at 99° C. for 5 min and hybridized to an oligonucleotide array overnight at 40° C. on a rotisserie at 40 rpm. All washes and staining were performed at room temperature. Oligonucleotide arrays were washed twice with 1×MES buffer [0.1 M 2-[N-Morpoline]ethanesulfonic acid (pH 6.7), 1 M NaCl, and 0.01% Triton X-100], and stained with staining solution [streptavidin R-phycoerythrin (20 $\mu$g/ml) (Molecular Probes) and acetylated bovine serum albumin (BSA) (1 mg/ml) in 2×MES] for 20 min on a rotisserie at 40 rpm. Following two washes with 1×NES, chips were incubated with antibody solution [biotinylated anti-streptavidin antibody (10 $\mu$g/ml) and BSA (1 mg/ml) in 2×MES] for 20 min on a rotisserie at 40 rpm. After two washes with 1×MES, chips were stained again with staining solution for 20 min. Oligonucleotide arrays were washed 6 times with 6×SSPET [0.9 M NaCl, 60 mM NaH$_2$PO$_4$, 6 mM EDTA (pH7.4), 0.01% Triton X-100] at 35° C. on a fluidics workstation (Affymetrix). Hybridization was detected by using a custom confocal scanner with a resolution of 110 pixels per feature (pixel size of 2.27 μM) and 560-nm filter.

Until the present invention, conserved human-mouse elements have been identified predominantly by aligning orthologous sequences. A commonly used threshold for defining an element as conserved in human-mouse sequence alignments is 70% identity over ≧100 base pairs (bp) in length. A fundamental difference between identifying conserved human-mouse elements by sequence alignments and by array analysis is that in the present invention the mouse sequence is not required. An algorithm was developed to detect evolutionarily conserved human chromosome 21-sequences using array data.

Data from the probe arrays were used to identify regions as potentially conserved between species. The identification procedure was developed by inspecting CONSEQ graphs of mouse DNA. This program allowed conformance to be computed over varying window sizes, with different amounts of overlap between the windows. CONSEQ also allowed the scientists to examine the reference sequence, the called cross-species sequence, and the location of repeats that were tiled on the probe arrays. Based on this evidence, it was determined that windows of 30 base pairs with an overlap of 10 base pairs that had conformance of 60% or higher showed strong similarity between human and mouse, except in cases where the window was close to or within a repeat or a region of low complexity. By inspection, it was determined that windows that were within 20 base pairs of a repeat sometimes showed spuriously high conformance. Likewise, inspection of windows with high conformance led to the decision that windows in which the reference sequence had either (a) 50% or more of a single base (either A, G, T, or C) or (b) 67% or more of a single base within any sub-window of 15 base pairs within the 30-base pair window (i.e., 10 or more out of 15), would sometimes show high conformance. Such sequences of low local complexity were considered not of interest, and were therefore not classified as potentially conserved. Finally, inspection of CONSEQ graphs led to the conclusion that nearby windows with high conformance were likely to be parts of the same potentially-conserved element. For example, there were clear cases where an exon was conserved and most, but not all, windows covering that exon showed high conformance. Thus, it was determined that regions of 120 base pairs or less between potentially conserved-windows would also be declared as potentially conserved.

The procedure for determining potentially conserved-regions was a multi-step process. The first step computed conformance for all 30-base pair windows (with 10-base pair overlap). In other words, the conformance was computed for base pairs 1–30, 21–50, 41–70, and so on, as the percent of probes matching the reference sequence (of the 60 probes—30 for the Watson strand, 30 for the Crick strand). Next, the distance of each window from the nearest known repeat was computed, using the output from RepeatMasker run on the reference sequence. Then the maximum frequency of any base in the reference sequence corresponding to each window was computed. For example, if in the first 30 base pairs of the reference sequence there were 10 A's, 8 C's, 7 G's, and 5 T's, then the maximum frequency would be 10. Finally, the maximum frequency of any base within a sub-window of 15 base pairs within the reference sequence was computed for each window. For the first window (base pairs 1–30 of the reference sequence), the 16 sub-windows would be base pairs 1–15, 2–16, . . . , 16–30; within each of the 16 sub-windows, the maximum frequency of any single base was computed, then the final result was the maximum of those 16 values. After these statistics were computed, windows were classified as potentially conserved for which (a) conformance was at least 60%, (b) nearest repeat was more than 20 base pairs away, (c) maximum single-base frequency was less than 50%, and (d) maximum single-base frequency for any 15-base pair sub-window was less than 67%. Then, for all potentially-conserved windows within 120 base pairs of another potentially-conserved window, the windows between them were also classified as potentially conserved. So, for example, if the window from base pairs 41–70 was potentially conserved, and the next potentially-conserved window was from base pairs 161–190, the windows at base pairs 61–90, 81–110, . . . , and 141–170 were also classified as potentially conserved. Finally, from the collection of potentially-conserved windows, the potentially-conserved contiguous regions were computed. Thus, if windows from base pairs 201–230, 221–250, and 241–270 were potentially conserved (but windows before and after were not), the region from base pairs 201–270 was classified as potentially conserved.

Once the identity parameters were determined, labeled mouse and dog sequences were incubated with the arrays. If the perfect match probe had greater fluorescent intensity than the corresponding mismatch probes, the nucleotide under interrogation was referred to as "conforming" to the human reference sequence. To identify conserved regions, 30-nucleotide (nt) windows (with 10 nt overlap with neighboring windows) were examined and the conformance of the Crick and Watson strands were averaged. For example, if in a 30-nt window 75% of the Crick strand nucleotides and 85% of the Watson strand nucleotides conformed to the reference sequence, the window would have a reported conformance of 80%.

Empirically-derived criteria were used to define a conserved element as a sequence with ≧60% conformance and ≧30 bp in length. The goal was to develop stringent criteria so that the resulting set of conserved elements would have high specificity (low false positive rate) with correspondingly lower sensitivity (higher false negative rate). To estimate the false positive rate, 10 chromosome 21 arrays (~600 kb) were hybridized with non-orthologous mouse DNA. Only 7 of the 30-nt windows had a conformance of ≧60%, of which 3 were low complexity sequences (a high percentage of a single base). Based on these results low complexity sequences were excluded as conserved elements. The same 600 kb segment of chromosome 21 sequence was hybridized with orthologous mouse DNA and by comparing the number of base pairs called conserved with non-orthologous versus orthologous mouse DNA, the false positive rate was estimated to be ~1%. When these rules were used to analyze 4 arrays containing ~240 kb of chromosome 21 sequence hybridized with non-orthologous dog DNA, not a single 30-nt window was identified as conserved.

The false negative rate was estimated by determining the percentage of exons the arrays failed to detect for twenty-two chromosome 21 genes with known mouse orthologs that have previously been sequenced. Human chromosome 21 sequence was searched against the GenBank database (November 2000) restricted to mouse using BLAST (default parameters). The matches of the following genes were inspected to ensure that only those corresponding to human-mouse orthologs were used: SAMSN-1, CXADR, BTG3, PRSS7, NCAM2, GABPA, APP, CCT8, BACH1, CLDN8, IFNAR2, IL10RB, GART, CBR1, CLDN14, SIM2, DSCAM, BACE2, PKNOX1, PFKL, SMT3H1, COL6A2. Exonic sequences in regions not analyzed by the oligonucleotide arrays were not used to calculate the false negative rate. The twenty-two genes were chosen to represent coding elements along the entire length of chromosome 21 with varying degrees of similarity between the human and mouse orthologs. One hundred and ninety exons had electronic matches using the BLAST algorithm and a cutoff of $E \leq 10^{-5}$ (where E is the expected value). After hybridizing the mouse BACs with the arrays and analyzing the data, 74% of the 190 electronic matches were identified as conserved elements in the analysis (see Table 1).

TABLE 1

| Expect score | # of BLAST matches | % identified by array | BLAST length (bp) | Total bp (%) overlap | BLAST % ID | Array % CON |
|---|---|---|---|---|---|---|
| $10^{-10}$ to $10^{-05}$ | 20 | 50 | 73 | 658 (42) | 88 | 71 |
| $10^{-20}$ to $10^{-10}$ | 47 | 55 | 90 | 2359 (41) | 89 | 72 |
| $10^{-30}$ to $10^{-20}$ | 40 | 72 | 126 | 3472 (45) | 89 | 72 |
| $10^{-40}$ to $10^{-30}$ | 24 | 79 | 151 | 2799 (51) | 89 | 68 |
| $10^{-60}$ to $10^{-40}$ | 29 | 90 | 169 | 4390 (54) | 90 | 69 |
| less than $10^{-60}$ | 30 | 100 | 322 | 9652 (49) | 90 | 65 |
| Total | 190 | 74 | 152 | 23330 (49) | 89 | 69 |

An estimation of the false negative rate The electronic matches of 190 exons were divided into 6 classes based on their Expect scores
# of BLAST matches = the number of electronic matches in the class.
% identified by array = the percent of electronic matches in the class that were identified as conserved elements by the array analysis,
BLAST length (bp) = the mean length in base pairs of the electronic matches in the class,
Total bp (%) overlap = for the conserved elements identified by both BLAST and the array —the total number of base pairs in the electronic matches and the percent of those base pairs identified by the array.
BLAST % ID = the mean percent identity of the electronic matches in class,
Array % CON = the mean percent conformance of the base pairs identified by both BLAST and the array.

The majority of the electronic matches missed were short (mean BLAST length $\leq 90$ bp); only 54% of the matches with $E \geq 10^{-20}$ were identified versus 85% of the matches with $E \leq 10^{-20}$. These data were also used to gauge how percent conformances and lengths of conserved elements identified by arrays compare with percent identities and lengths of conserved elements identified by sequence alignments. For the 140 conserved elements found by both BLAST and array analyses, the mean percent identities and percent conformances were 89% and 69%, respectively. Forty-nine percent of the base pairs present in the 140 electronic matches were represented in the conserved elements identified by the arrays. Thus the stringent criteria used in this analysis to minimize the number of false positives results in an underestimation of the number of conserved human-mouse elements and the elements that are found are shorter in length than those identified by sequence alignments. Chromosome 21 sequence and biological annotations were retrieved from GenBank in 106 segments, most of which are 340 kb size and have 1-kb overlap with neighboring segments (M. Hattori et al., Nature 405:311 (2000)).

All of chromosome 21-sequence, except for interspersed repeats identified by RepeatMasker was tiled on the arrays.

The percentage of human chromosome 21 analyzed was defined as the number of tiled base pairs hybridized to orthologous mouse DNA (16,580,114), divided by the total number of non-repetitive base pairs tiled on the arrays (22,490,347)=~74%. In the ~74% of chromosome 21 analyzed by hybridization with orthologous mouse DNA, the arrays identified 3,398 conserved elements, of which 895 overlapped exons of known 21q genes (as annotated in GenBank files). The identified elements hybridized with mouse DNA, are noncontiguous and span ~30 Mb. The unidentified, conserved remaining 2,503 elements were examined to determine if they had similarities to known exonic sequences: 135 were exons of chromosome 21 genes (missing GenBank annotations), 34 matched genes not previously assigned to chromosome 21, and 77 matched ESTs (many are likely alternatively spliced exons). The remaining 2,257 were not in identified exons (NIEs). In the segment of chromosome 21 analyzed, ~1.6% of the base pairs outside of repetitive elements are conserved (260,226 bp) of which 56% corresponds to the 2,257 NIEs and 44% corresponds to the 1,141 identified exons (IEs).

TABLE 2

| | # of elements | # of bps | % of hyb'd bps | Length (bp) | | | |
|---|---|---|---|---|---|---|---|
| | | | | Mean | S.D. | Min. | Max. |
| $\geq 30$ bp | | | | | | | |
| Total | 3398 | 260226 | 1.6 | 76 | 109 | 30 | 2690 |
| NIE | 2257 | 145010 | 0.9 | 64 | 78 | 30 | 950 |
| IE | 1141 | 115216 | 0.6 | 101 | 150 | 30 | 2690 |
| $\geq 50$ bp | | | | | | | |
| Total | 1478 | 202623 | 1.2 | 137 | 144 | 50 | 2690 |
| NIE | 762 | 100160 | 0.7 | 131 | 105 | 50 | 950 |
| IE | 716 | 102463 | 0.6 | 143 | 176 | 50 | 2690 |

The number and sizes of human-mouse conserved elements $\geq 30$ bp = analysis of all elements fitting criteria of conservation, $\geq 50$ bp = analysis of the subset of conserved elements that are greater than or equal to 50 base pairs in length; Total = both NIE and IE classes, # of elements = number of conserved elements identified, # of bps = the number of base pairs covered by all the conserved elements, % of hyb'd bps = the percent of the hybridized tiled base pairs which are conserved. For the length data Mean = mean length in base pairs of conserved elements, S.D = standard deviation, Min. = length of the shortest element, Max. = length of the longest element. For detailed analysis, see Web Table 4

Since long human-mouse elements are more likely to be actively conserved than shorter ones, the set of elements analyzed were those $\geq 50$ nucleotides in length. Although this represents only 43% of all human-mouse elements because those eliminated were short, the amount of chromosome 21 sequence considered conserved is only reduced by 22%. In this set of longer elements, the numbers and lengths of the NIEs and IEs is similar (Table 2). These data suggest that known genes compose only half of the sequences on chromosome 21 conserved between humans and mice.

Chromosome 21 contains 225 genes, of which 127 correspond to known genes and 98 represent genes predicted in silico. These predictions were compared to the human-mouse conservation results obtained by the methods of the present invention. Sixty-nine predictions were examined; 14 of the 15 class 1 (those with similarity to a previously identified gene or ORF) and 13 of the 54 class 2 (those based solely on spliced EST matches and/or consistent exon predictions) predictions had at least one exon conserved. These results indicate that class 1 predictions are supported by human-mouse conservation whereas the majority of class 2 predictions are not.

The distribution of conserved human-mouse sequences on chromosome 21 was examined by calculating the percent of base pairs conserved in consecutive 300-kb intervals with 1-kb overlaps. The number of base pairs conserved in the intervals ranged from 0.1–4.16%. For the two intervals with the highest levels of conservation, one was dominated by IE elements and the other by NIE elements. These data suggests that the percentage of base pairs conserved in the 300-kb intervals is not directly correlated with known coding potential.

In the ~12% of 21q sequence hybridized with orthologous dog DNA (the number of tiled base pairs hybridized to orthologous dog DNA (2,597,732) divided by the total number of non-repetitive chromosome 21 base pairs tiled on the arrays (22,490,347)=~12%), 1,292 conserved elements were identified. Of these, 240 are IE and 1,052 are NIE elements. The arrays identified 1,292 conserved human-dog elements of which 197 overlapped exons of known chromosome 21 genes (as annotated in GenBank files). The remaining 1,095 conserved elements were compared against the GenBank nt (November 2000) and dbEST (January 2001) databases using BLAST (default parameters). Matches with expect values $\leq 10^{-5}$ and the words "genomic DNA" or "Chromosome 21" in the FASTA description line were excluded. Of the 1,095 elements, 10 were exons of known chromosome 21 genes (missing GenBank annotations), and 14 matched cDNAs not assigned to chromosome 21 at the time the sequence was released. FIGS. 3 and 4 show data obtained from human chromosome 21 sequence hybridized with syntenic dog sequence. FIG. 3 shows an enlarged view of a human 21q array hybridized with syntenic dog BAC DNA (top). Two 30 nucleotide intervals, one with high conformance between the human and dog sequences (left rectangle) and one with low conformance between human and dog sequences (right rectangle), are shown. For the conserved sequence with high conformance (97%), the 29 conforming nucleotides are shown. For the conserved sequence with low conformance (60%), the 18 conforming nucleotides are shown. FIG. 4 shows a CONSEQ plot of conserved regions identified by hybridization with syntenic dog sequences for a 26-kb interval on chromosome 21. Conserved elements (highlighted peaks) detected are shown relative to their position in the human reference sequence (horizontal axis), and their percent conformance (50–100%) is indicated on the vertical axis. The high conformance (97%) conserved sequence has been merged with neighboring conserved sequences to form a 200-nt conserved element. The low conformance (60%) conserved sequence is a 30-nt element. Small rectangles on the top line indicate the positions of interspersed repeats, which were not tiled on the arrays, therefore conformance information is absent.

The 21q.22 region hybridized with both mouse and dog DNA (~10% of 21q) was used to compare the human-mouse and human-dog conserved elements. (The number of tiled base pairs hybridized to both orthologous mouse and dog DNA (2,232,610), divided by the total number of non-repetitive chromosome 21 base pairs tiled on the arrays (22,490,347)=~10%. These base pairs are noncontiguous and span ~6 Mb in the 22q.22 region.) In this region, ~4.3% and ~1.3% of the base pairs outside of repetitive elements were conserved in the dog and mouse analyses, respectively (Table 3).

TABLE 3

| | IE | | | | | | NIE | | | | | |
|---|---|---|---|---|---|---|---|---|---|---|---|---|
| | | % of hyb'd | Length | | | | | % of hyb'd | Length | | | |
| | (n) | bps | Mean | S.D. | Min. | Max. | (n) | bps | Mean | S.D. | Min. | Max. |
| Total Dog | 219 | 1.1 | 112.3 | 108.9 | 30 | 710 | 956 | 3.2 | 74.6 | 94.1 | 30 | 1,250 |
| Dog/Mouse | 132 | 0.8 | 137.6 | 125.4 | 30 | 710 | 114 | 1.0 | 196.2 | 186.0 | 30 | 1,250 |
| Dog only | 87 | 0.3 | 73.9 | 60.5 | 30 | 370 | 842 | 2.2 | 58.2 | 56.0 | 30 | 410 |
| Total Mouse | 140 | 0.5 | 79.1 | 81.9 | 30 | 670 | 240 | 0.7 | 63.0 | 85.4 | 30 | 950 |
| Mouse/Dog | 129 | 0.5 | 81.0 | 84.0 | 30 | 670 | 120 | 0.5 | 90.7 | 113.2 | 30 | 950 |
| Mouse only | 11 | 0.0 | 57.3 | 47.6 | 30 | 190 | 120 | 0.2 | 35.3 | 16.9 | 30 | 130 |

A comparison of the number and lengths of human/dog and human/mouse conserved elements identified in ~10% of chromosome 21 Total Dog = all the human/dog elements; Dog/Mouse = the human/dog elements that overlap human/mouse elements, Dog only = the human/dog elements that do not overlap human/mouse elements, Total Mouse = all the human/mouse elements, Mouse/Dog = the human/mouse elements that overlap human/dog elements, Mouse only = the human/mouse elements that do not overlap human/dog elements The number of conserved elements identified (n) and the percent of the hybridized non-repetitive base pairs (% of hyb'd bps) covered by all the conserved elements, is given The number of elements in the Dog/Mouse and the Mouse/Dog groups are different because multiple elements in one analysis are equal to one element in the other. For the length data Mean = the mean length in base pairs of all conserved elements, SD = standard deviation of length, Min = length of the shortest element. Max = length of the longest element.

The dog analysis identified considerably more IEs and NIEs than the mouse analysis. The conserved elements (IEs and NIEs) identified in both analyses are usually longer suggesting a higher level of conservation than those identified in a single species. Unlike IEs that have clear function, the function of NMEs is unclear. NIEs present in all three species (human/dog/mouse), however are more likely to be conserved due to functional constraints than NIEs observed in only two species.

2. Evolutionarily Conserved Sequences on Human Chromosome 21 by Comparing Human Sequence to Primate Sequence Chromosome 21 was examined for evolutionarily conserved elements by hybridization of gorilla, chimpanzee and macaque sequences to human oligonucleotide arrays. Unlike the dog and mouse nucleic acid samples, the primate nucleic acid samples were prepared by long range PCR amplification of genomic DNA. Protocols much like the following were employed. Primers used for the amplification reaction were designed in the following way: a human chromosome 21 sequence was fed into the software program Repeat Masker which recognizes sequences that are repeated in the genome (i.e., Alu and Line elements). The repeated sequences are "masked" by the program by substituting the specific nucleotides of the sequence (A, T, G or C) with "Ns". The sequence output after this repeat mask substitution was then fed into a commercially available primer design program (Oligo 6.23) to select primers that were greater than 30 nucleotides in length, had melting temperatures of over 65° C. and had sequences chosen only from the non-repetitive regions. The designed primer output from Oligo 6.23 was then fed into a program which then "chose" primer pairs which would PCR amplify a given region of the genome but have minimal overlap. An illustrative protocol for long range PCR is as follows:

Reagents Used:
1. Expand™ Long Template PCR System from Boehringer Mannheim Cat.# 1681 834, 1681 842, or 1759 060.
2. 100 mM dNTP set from Life Technologies, Cat.# 10297-018.
3. Molecular Biology Grade Water from Bio Whittaker, Cat.# 16-001Y.
4. 1 M $MgCl_2$ from Sigma, Cat.# M 1028.

2 master mixes are required for each 50 μL PCR reaction: Separate Master Mix 1 was prepared for each template in 1.5 ml microfuge tubes on ice:
1. Master mix 1 (for 1 PCR reaction)
   Add Bio Whittaker water to a final volume of 19 μL
   2.5 μL 10 mM dNTP mix (containing dATP, dCTP, dGTP, and dTTP at 10 mM each) for a final concentration of 500 μM each dNTP
   50 ng DNA template
2. Master Mix 2 for all reactions (+1 extra) was then prepared and kept on ice:
   Master mix 2 (for 1 PCR reaction)
   Add Bio Whittaker water to a final volume of 25 μL
   5 μL 10×PCR buffer 3 (which contains 22.50 mM $MgCl_2$)
   2.5 μL 10 mM $MgCl_2$ (for a final $MgCl_2$ concentration of 2.75 mM)
   0.75 μL enzyme mix (add last)

Six microliters of premixed primers (containing 2.5 M of each primer) were added to 8 strip PCR tubes on ice. Next, 19 L of Master Mix 1 was added to appropriate tubes, then 25 L of Master Mix 2 was added to each tube. The tubes were capped, mixed, centrifuged briefly and returned to ice. At this point, the PCR cycling was begun according to the following program: step 1: 94° C. for 3 min to denature template; step 2: 94° C. for 30 sec; step 3: annealing for 30 sec at a temperature appropriate for the primers used; step 4: elongation at 68° C. for 1 min/kb of product; step 5: repetition of steps 2–4 38 times for a total of 39 cycles; step 6: 94° C. for 30 sec; step 7: annealing for 30 sec; step 8: elongation at 68° C. for 1 min/kb of product plus 5 additional minutes; and step 9: hold at 4° C. Alternatively, a two-step PCR would be performed: step 1: 94° C. for 3 min to denature template; step 2: 94° C. for 30 sec; step 3: annealing and elongation at 68° C. for 1 min/kb of product; step 4: repetition of steps 2–3 38 times for a total of 39 cycles; step 5: 94° C. for 30 sec; step 6: annealing and elongation at 68° C. for 1 min/kb of product plus 5 additional minutes; and step 7: hold at 4° C.

Human chromosome 21 sequence was used to design high-density arrays consisting of 25-mer oligonucleotides (probes) (see, for example, M. Chee, et al., Science 274: 610 (1996); S. P. Fodor, et al., 767 (1991); A. C. Pease, et al., Proc. Natl. Acad. Sci. USA 91:5022 (1994)) and WO 95/11995, WO 92/10092, or U.S. Pat. Nos. 5,143,854; 5,384,261; 5,405,783; 5,412,087; 5,424,186; 5,445,934; 5,744,305; 5,800,992; 6,040,138; 6,040,193; all of which are incorporated herein by reference for all purposes). Four probes were designed to interrogate each nucleotide present in chromosome 21 sequence, one probe complementary to the sequence and three mismatch probes identical to the complementary probe except for the nucleotide at the central position (the $13^{th}$ position) under interrogation. At this central position, each mismatch probe contains one of the bases not identical to the perfect match probe.

DNA labeling and hybridization to arrays was performed as described in if D. G. Wang et al., Science 280: 1077 (1998) with minor modifications. The amplified genomic DNA was fragmented with deoxyribonuclease (Dnase) 1 and labeled with biotin with terminal deoxynucleotidyl transferase as described in the first Example. Next, labeled DNA samples were denatured in hybridization buffer and hybridized to an oligonucleotide array overnight at 40° C. on a rotisserie at 40 rpm. Hybridization was detected by using a custom confocal scanner with a resolution of 110 pixels per feature (pixel size of 2.27 μM) and 560-nm filter.

If, upon incubation of the labeled gorilla, chimp or macaque samples with the arrays the perfect match probe had greater fluorescent intensity than the corresponding mismatch probes, the nucleotide under interrogation was referred to as "conforming" to the human reference sequence. To identify conserved regions, 30-nucleotide (nt) windows (with 10 nt overlap with neighboring windows) were examined and the conformance of the Crick and Watson strands were averaged. For example, if in a 30-nt window 75% of the Crick strand nucleotides and 85% of the Watson strand nucleotides conformed to the reference sequence, the window would have a reported conformance of 80%.

The results of scans performed on four substrate-bound oligonucleotide arrays are shown in FIG. 5. The sequence of the probes on these arrays is based on human genomic sequence from chromosome 21. Four identical arrays were hybridized with human, gorilla, chimpanzee or macaque amplified genomic DNA samples. Each column of the array has a group or set of four probes, each probe having a different base in the interrogation position. The sequence of the base in the interrogation position is, from top to bottom, A-C-G-T. A "street" or unoccupied position is inserted in the column in the fifth position, then another set of four probes occurs. In this set of four probes, the same scheme is used; each probe has a different base in the interrogation position and the sequence of the base in the interrogation position is, from top to bottom, A-C-G-T, a street position is inserted and so on. The horizontal rows correspond to the reference sequence as described above. In looking at the scans, one can see that the pattern of hybridization is very similar between the human, gorilla and chimp sequences. The patterns of hybridization of the human and macaque samples have enough similarity to detect conserved bases, but the sequence divergence is becoming more pronounced. Also this data shows that sequence can be determined quickly in regions of both the gorilla and the chimp genomes. Thus, the present invention is useful for rapid sequencing of regions of high conformance between sequences when one of the sequences is known.

Detailed results of a 100 kb interval of the SIM2 region of human chromosome 21 is seen in FIG. 6. Mouse and dog CONSEQ plots are shown at the bottom of the figure. Conserved elements are highlighted relative to their position in the human reference sequence horizontal axes, and their percent conformance (0–100%) are indicated on the vertical axes. Peaks with ≧60% conformance are shown. Shaded peaks not highlighted have ≧60% conformance but are low complexity or are close to a repeat. The locations of Gen-Bank annotated single-minded 2 (SIM2) exons (rectangles), elements identified as coding sequences by database searches (white rectangles with black outline), and chromosome 21 cross-species markers (black with highlighted background) are shown. Small rectangles at the top line of the plots indicate the positions of interspersed repeats, which were not tiled on the arrays, and therefore conformance information is absent. Note that the baseline for sequence similarity in the plot for dog is set at 50% and for mouse is set at 40%.

In addition to the dog and mouse plots, FIG. 6 contains CONSEQ plots of conserved regions between human and gorilla, macaque and chimp sequences for >14 kb intervals (interval 184 to 199 is shown for gorilla and macaque, and interval 228 to 244 is shown for gorilla and chimp). In the primate plots, the baseline for sequence similarity is set at 0%. Note that conformance in the gorilla and chimp is >75–80% for a large number of bases in these intervals, and that conformance for the macaque is also high, particularly when compared to the conformance of these same intervals in the mouse and dog plots below. There are, however, segments in the macaque sequence (at approximately positions 189 to 194) and in the chimp sequence (at approximately positions 234 to 237) where the conformance to both the human sequence and the gorilla sequence is low. Clearly, areas of conformance are of interest in species comparisons, as these are the regions of a genome that have been conserved over time. However, areas of nonconformance are also of interest in closely-related species or organisms. These are the regions that are most likely to contain the genetic information that differentiates the organisms.

The present invention provides greatly improved methods for recognizing functional sequences in a genome—both in coding regions and in non-coding regions—by employing techniques that allow the comparison of the genomic sequence of one organism to another organism to identify nucleic acid sequences that are conserved between the two organisms. The present invention particularly is powerful as it allows such comparison without having to know the nucleic acid sequence of both organisms as is necessary in prior art comparison methods—in the present invention, knowledge of the nucleic acid sequence of only one of the organism is necessary. In addition, the present invention allows even greater accuracy for determining functional regions of the genome of a first species, as it can be used to compare sequences between a first species (where the nucleic acid sequence is known) and a second species (where the nucleic acid sequence is not known), and then between the first species and a third species (where the nucleic acid sequence is not known). Conversely, the present invention provides methods for identifying species-differentiating sequences, by employing techniques that compare genomic sequence from very closely-related organisms. The present invention particularly is powerful for this purpose as it allows such comparison without having to know the nucleic acid sequence of both organisms as is necessary in prior art comparison methods.

3. Generation of Primers for Human/Mouse Sequence Alignments for Amplification of Orthologous Regions from the Genomic DNA of Other Mammals Primers were generated for sequence alignments of human and mouse for utilization in the amplification of orthologous regions from the genomic DNA of other mammals. A skilled artisan recognizes that the detailed descriptions described are generally applicable to other specific examples.

For the chromosome 21 29.38 to 33.90 region: wafer 5 contains from Segment 55 205-kb to Segment 68 240-kb. This corresponds to chr21:29380000–33900000. The human/mouse alignments were downloaded and only chr.21.xls were kept. The mouse traces with alignments greater than or equal to 300 bp and 80% were retained and blasted against the masked chromosome 21 sequence (BigMaskedSequence).

A skilled artisan recognizes that there are a variety of criteria which are important regarding design of primers for polymerase chain reaction. The specific example provided herein is merely exemplary, and a skilled artisan is aware which parameters to alter to obtain the desired primer. Herein, primers were chosen (chr21 29.38 to 33.90 primer) based on at least some of the following criteria. Primers which were chosen were not degenerate. Primers were based on the human sequence, given the fact that other mammals are more likely to have greater similarity at the nucleotide level to humans than to mouse. Primers were chosen to have about 50% GC content, although the GC content may be variable. Furthermore, primers were chosen to minimize human/mouse mismatches. That is, to minimize the percent of human/mouse mismatches, primers were generally longer than normal primer pairs used for PCR amplification, which are generally about 20–25 nucleotides in length.

PCR conditions are also variable, and a skilled artisan recognizes how alter the conditions to achieve the desired result. A greater than typical amount of primers were used, such as 100 $\mu$M instead of 10 $\mu$M. This is to account for the fact that some of the negative effects of mismatch can be compensated for by increasing the relative primer concentrations. Furthermore, a two step process was used. The polymerase chain reaction cycles began at a higher temperature of annealing and proceeded for a limited set of cycles (for example, about 10 cycles). This was followed by about 30 cycles using a lower annealing temperature.

It is to be understood that the above description is intended to be illustrative and not restrictive. Many embodiments will be apparent to those skilled in the art upon reviewing the above description. The scope of the invention should, therefore, be determined not with reference to the above description, but should instead be determined with reference to the appended claims, along with the full scope of equivalents to which such claims are entitled.

What is claimed is:

1. A method for identifying a region as an evolutionarily conserved sequence, comprising the steps of:
   collecting a plurality of hybridization intensities wherein each of said intensities reflects the hybridization of one of a plurality of probes to a sample nucleic acid sequence from a first organism, wherein said probes are complementary and non-complementary to a known nucleic acid sequence from a second organism, wherein said probes are arrayed on a substrate and wherein each of said probes is at a known location on said substrate;
   identifying bases of said sample nucleic acid sequence according to said hybridization intensities;
   using said identified bases of said sample nucleic acid sequence and said known nucleic acid sequence to calculate a conformance between said known nucleic acid sequence and said sample nucleic acid sequence across said region of said sample nucleic acid sequence;
   measuring the distance from said region to the nearest repeat sequence;
   measuring the maximum single base frequency within said region; and
   measuring the maximum single base frequency in each of a set of subregions within said region, whereby if said conformance is at least 60%, said distance from said region to said nearest repeat sequence is more than 20 base pairs, said maximum single base frequency within said region is less than 50%, and said maximum single base frequency in each of said set of subregions within said region is less than 67%, said region is an evolutionarily conserved sequence.

2. The method of claim 1, wherein said probes are sets of four probes where one probe of said probe set is perfectly complementary and thereby a perfect match probe to said known nucleic acid sequence, and three probes of said probe set are non-complementary and thereby mismatch probes to said known nucleic acid sequence.

3. The method of claim 2, wherein said non-complementary probes differ from said perfectly complementary probe of said probe set by one base.

4. The method of claim 3, wherein said one base is a base located at or near a central position of said probe.

5. The method of claim 1, wherein said sample nucleic acid sequence has been amplified by the polymerase chain reaction.

6. The method of claim 2, wherein said conformance is calculated by determining a percentage of probe sets for which the perfect match probe had a greater fluorescent intensity than any of the mismatch probes for said region of said sample nucleic acid sequence.

7. The method of claim 6, wherein conformance is calculated for a plurality of said regions, wherein said regions are overlapping, moving windows of base pairs.

8. The method of claim 7, wherein said windows are between about 20 and 150 base pairs in length.

9. The method of claim 7, wherein said overlap of said windows is between about 5 and about 75 base pairs in length.

10. The method of claim 1, wherein said region is a 30 base pair window.

11. The method of claim 1, wherein said set of subregions is a set of 15 base pair sub-windows within said region.

12. The method of claim 1, wherein two regions are identified as evolutionarily conserved sequences, further comprising identifying as an evolutionarily conserved sequence a nucleic acid sequence of said sample nucleic acid that is located between said two regions, wherein said two regions are within 120 base pairs of one another.

* * * * *

UNITED STATES PATENT AND TRADEMARK OFFICE
CERTIFICATE OF CORRECTION

PATENT NO.        : 6,963,805 B2
APPLICATION NO. : 09/972595
DATED             : November 8, 2005
INVENTOR(S)       : Frazer et al.

Page 1 of 1

It is certified that error appears in the above-identified patent and that said Letters Patent is hereby corrected as shown below:

Column 1, line 5, insert:

--STATEMENT OF GOVERNMENT INTEREST
This invention was made with government support under NIH Grant No. 7R01GM57482-04. As such, the United States government has certain rights in this invention.--.

Signed and Sealed this

Eleventh Day of July, 2006

JON W. DUDAS
*Director of the United States Patent and Trademark Office*